US012582483B2

(12) United States Patent
Moctezuma de la Barrera et al.

(10) Patent No.: US 12,582,483 B2
(45) Date of Patent: Mar. 24, 2026

(54) TRACKING APPARATUS FOR TRACKING A PATIENT LIMB

(71) Applicant: MAKO Surgical Corp., Weston, FL (US)

(72) Inventors: José Luis Moctezuma de la Barrera, Freiburg (DE); Christine Merz, Freiburg (DE); Peter Hess, Habsburg (CH)

(73) Assignee: MAKO Surgical Corp., Weston, FL (US)

( * ) Notice: Subject to any disclaimer, the term of this patent is extended or adjusted under 35 U.S.C. 154(b) by 317 days.

(21) Appl. No.: 17/883,667

(22) Filed: Aug. 9, 2022

(65) Prior Publication Data

US 2023/0047385 A1 Feb. 16, 2023

Related U.S. Application Data

(60) Provisional application No. 63/231,308, filed on Aug. 10, 2021.

(51) Int. Cl.
A61B 34/20 (2016.01)

(52) U.S. Cl.
CPC ...... *A61B 34/20* (2016.02); *A61B 2034/2051* (2016.02); *A61B 2034/2055* (2016.02);
(Continued)

(58) Field of Classification Search
CPC ..... A61B 8/4227; A61B 34/30; A61B 5/6844; A61B 8/4254; A61B 2034/2063
See application file for complete search history.

(56) References Cited

U.S. PATENT DOCUMENTS 5,810,008 A 9/1998 Dekel et al.
6,106,464 A 8/2000 Bass et al.
(Continued)

FOREIGN PATENT DOCUMENTS

CA 2813976 A1 4/2012
CA 2845044 A1 2/2013
(Continued)

OTHER PUBLICATIONS

English language abstract for JP 2016-202974 A extracted from espacenet.com database on Aug. 10, 2022, 2 pages.
(Continued)

*Primary Examiner* — Christopher Koharski
*Assistant Examiner* — Aminah Asghar
(74) *Attorney, Agent, or Firm* — Howard & Howard Attorneys PLLC

(57) ABSTRACT

A tracking apparatus for tracking a bone of a patient limb is provided. The tracking apparatus includes a body configured to couple to the patient limb. The body includes first and second arms each including an exterior and opposing interior surface and opposing sides connecting the exterior and interior surfaces. The tracking apparatus also includes a wing portion extending from one of the sides of the first or second arm, the wing portion sharing the interior surface of the first or second arm. The tracking apparatus also includes one or more ultrasonic sensors coupled to the interior surface of the body and the interior surface of wing portion, the one or more ultrasonic sensor being configured to transmit ultrasonic waves to and receive ultrasonic waves from the bone. The tracking apparatus also includes one or more trackable elements coupled to the body and the wing portion.

20 Claims, 17 Drawing Sheets

(52) U.S. Cl.
      CPC ................. *A61B 2034/2063* (2016.02); *A61B 2034/2065* (2016.02); *A61B 2034/2072* (2016.02); *A61B 2560/0223* (2013.01)

(56)                    References Cited

U.S. PATENT DOCUMENTS

| | | | |
|---|---|---|---|
| 6,122,538 | A | 9/2000 | Sliwa, Jr. et al. |
| 6,190,320 | B1 | 2/2001 | Lelong |
| 6,203,497 | B1 | 3/2001 | Dekel et al. |
| 7,657,298 | B2 | 2/2010 | Moctezuma de la Barrera et al. |
| 7,938,777 | B2 | 5/2011 | Amiot et al. |
| 7,945,105 | B1 | 5/2011 | Jaenisch |
| 7,949,386 | B2 | 5/2011 | Buly et al. |
| 8,082,022 | B2 | 12/2011 | Moctezuma de la Barrera et al. |
| 8,108,072 | B2 | 1/2012 | Zhao et al. |
| 8,109,877 | B2 | 2/2012 | Moctezuma de la Barrera et al. |
| 8,152,726 | B2 | 4/2012 | Amiot et al. |
| 8,274,377 | B2 | 9/2012 | Smith et al. |
| 8,288,721 | B2 | 10/2012 | Morris et al. |
| 8,313,490 | B2 | 11/2012 | May |
| 8,444,564 | B2 | 5/2013 | Mahfouz et al. |
| 8,509,503 | B2 | 8/2013 | Nahum et al. |
| 8,536,527 | B2 | 9/2013 | Morris et al. |
| 8,540,638 | B2 | 9/2013 | Gourevitch |
| 8,675,939 | B2 | 3/2014 | Moctezuma de la Barrera |
| 8,771,188 | B2 | 7/2014 | Schers et al. |
| 8,939,909 | B2 | 1/2015 | Wegner |
| 9,008,757 | B2 | 4/2015 | Wu |
| 9,119,655 | B2 | 9/2015 | Bowling et al. |
| 9,199,096 | B2 | 12/2015 | Lewis, Jr. |
| 9,211,164 | B2 | 12/2015 | Moctezuma de la Barrera et al. |
| 9,420,999 | B2 | 8/2016 | Wegner |
| 9,423,362 | B2 | 8/2016 | Sossong et al. |
| 9,572,548 | B2 | 2/2017 | Moctezuma de la Barrera |
| 9,588,064 | B2 | 3/2017 | Kumnadi et al. |
| 9,592,096 | B2 | 3/2017 | Maillet et al. |
| 9,639,973 | B2 | 5/2017 | Bai et al. |
| 9,642,572 | B2 | 5/2017 | Mahfouz et al. |
| 9,707,043 | B2 | 7/2017 | Bozung |
| 9,746,580 | B2 | 8/2017 | Hayes et al. |
| 9,784,859 | B2 | 10/2017 | Blanpied et al. |
| 9,817,150 | B2 | 11/2017 | Sossong |
| 9,841,530 | B2 | 12/2017 | Blanpied et al. |
| 9,844,359 | B2 | 12/2017 | Wegner |
| 9,851,311 | B2 | 12/2017 | Sossong et al. |
| 9,872,667 | B2 | 1/2018 | Wegner |
| 9,895,135 | B2 | 2/2018 | Pelissier et al. |
| 9,915,626 | B2 | 3/2018 | Blanpied et al. |
| 9,924,923 | B2 | 3/2018 | Mauldin, Jr. et al. |
| 9,939,537 | B2 | 4/2018 | Sossong |
| 10,042,079 | B2 | 8/2018 | Patnaik |
| 10,067,260 | B2 | 9/2018 | McKenney et al. |
| 10,166,002 | B2 | 1/2019 | Schers et al. |
| 10,213,128 | B2 | 2/2019 | Mahfouz |
| 10,251,622 | B2 | 4/2019 | Tesic et al. |
| 10,335,116 | B2 | 7/2019 | Boctor et al. |
| 10,426,429 | B2 | 10/2019 | Kruse et al. |
| 10,512,451 | B2 | 12/2019 | Mahfouz |
| 10,517,568 | B2 | 12/2019 | Wasielewski |
| 10,531,926 | B2 | 1/2020 | Roessler |
| 10,561,394 | B2 | 2/2020 | Wang et al. |
| 10,653,389 | B2 | 5/2020 | Kiyan et al. |
| 11,004,561 | B2 | 5/2021 | Mahfouz et al. |
| 11,123,040 | B2 | 9/2021 | Mahfouz et al. |
| 11,246,719 | B2 | 2/2022 | Kilng et al. |
| 11,342,071 | B2 | 5/2022 | Mahfouz et al. |
| 2003/0195420 | A1 | 10/2003 | Mendlein et al. |
| 2004/0011088 | A1 | 1/2004 | Rebouillat et al. |
| 2004/0064046 | A1 | 4/2004 | Shehada |
| 2004/0068263 | A1 | 4/2004 | Chouinard et al. |
| 2007/0239153 | A1 | 10/2007 | Hodorek et al. |
| 2008/0071195 | A1 | 3/2008 | Cuellar et al. |
| 2009/0018445 | A1 | 1/2009 | Schers et al. |
| 2011/0216945 | A1 | 9/2011 | Jaenisch |
| 2012/0029358 | A1 | 2/2012 | Lin |
| 2012/0330429 | A1 | 12/2012 | Axelson, Jr. et al. |
| 2013/0041260 | A1 | 2/2013 | Schmidt et al. |
| 2013/0144135 | A1 | 6/2013 | Mahfouz et al. |
| 2013/0211259 | A1 | 8/2013 | Komistek et al. |
| 2013/0253379 | A1 | 9/2013 | Mahfouz et al. |
| 2014/0163375 | A1 | 6/2014 | Wasielewski |
| 2014/0221825 | A1 | 8/2014 | Mahfouz et al. |
| 2014/0276949 | A1 | 9/2014 | Staunton et al. |
| 2014/0303538 | A1* | 10/2014 | Baym .................. A61B 5/6812 |
| | | | 602/23 |
| 2014/0371577 | A1 | 12/2014 | Maillet et al. |
| 2015/0051490 | A1 | 2/2015 | McKinnon et al. |
| 2015/0245802 | A1 | 9/2015 | Sossong et al. |
| 2015/0246244 | A1 | 9/2015 | Sossong et al. |
| 2015/0374334 | A1 | 12/2015 | Klock et al. |
| 2016/0029997 | A1 | 2/2016 | Moctezuma de la Barrera et al. |
| 2016/0061752 | A1 | 3/2016 | Kurnadi et al. |
| 2016/0104290 | A1 | 4/2016 | Patnaik |
| 2016/0116630 | A1 | 4/2016 | Sossong |
| 2016/0242736 | A1 | 8/2016 | Freiburg et al. |
| 2016/0270763 | A1 | 9/2016 | Hayes et al. |
| 2016/0356913 | A1 | 12/2016 | Sossong et al. |
| 2017/0021171 | A1* | 1/2017 | Perez ................. A61N 1/36034 |
| 2017/0100092 | A1 | 4/2017 | Kruse et al. |
| 2017/0202629 | A1 | 7/2017 | Maillet et al. |
| 2017/0232277 | A1 | 8/2017 | Hall et al. |
| 2017/0245830 | A1 | 8/2017 | Netravali et al. |
| 2017/0281122 | A1 | 10/2017 | Mahfouz et al. |
| 2017/0296091 | A1 | 10/2017 | Mahfouz |
| 2017/0296115 | A1 | 10/2017 | Mahfouz et al. |
| 2017/0296124 | A1* | 10/2017 | Creemers ........... A61B 5/02438 |
| 2017/0311923 | A1* | 11/2017 | Saberi .................. A61B 8/4427 |
| 2017/0347991 | A1 | 12/2017 | Mahfouz |
| 2018/0153518 | A1 | 6/2018 | Wegner |
| 2018/0206817 | A1 | 7/2018 | Wegner |
| 2018/0289425 | A1* | 10/2018 | Li ....................... A61B 5/1127 |
| 2019/0069882 | A1 | 3/2019 | Moctezuma de la Barrera et al. |
| 2019/0151192 | A1 | 5/2019 | Yamashita |
| 2019/0231317 | A1* | 8/2019 | Anthony ................ A61B 8/429 |
| 2020/0000436 | A1 | 1/2020 | Mahfouz |
| 2020/0005552 | A1 | 1/2020 | Furst |
| 2020/0029933 | A1 | 1/2020 | Wegner |
| 2020/0060735 | A1 | 2/2020 | Chang et al. |
| 2020/0205898 | A1* | 7/2020 | Hampp .................. A61B 34/25 |
| 2021/0259781 | A1* | 8/2021 | Forstein ................. A61B 5/742 |
| 2021/0290313 | A1* | 9/2021 | Cerda-Carvajal ...... A61B 34/20 |
| 2021/0378631 | A1 | 12/2021 | Mahfouz et al. |
| 2021/0393427 | A1* | 12/2021 | Mirza .................. A61B 5/6812 |
| 2022/0000395 | A1* | 1/2022 | Lai ......................... A61B 5/389 |
| 2022/0215947 | A1 | 7/2022 | Mahfouz et al. |

FOREIGN PATENT DOCUMENTS

| | | | |
|---|---|---|---|
| CA | 2852233 | A1 | 4/2013 |
| CA | 2906476 | A1 | 9/2014 |
| CA | 2906506 | A1 | 9/2014 |
| CA | 2751422 | C | 10/2017 |
| CA | 2864045 | C | 3/2018 |
| CA | 2900264 | C | 7/2018 |
| CA | 2978543 | C | 3/2019 |
| CA | 2977574 | C | 7/2019 |
| CA | 2984069 | C | 4/2021 |
| CA | 2807288 | C | 10/2021 |
| EP | 2358276 | B1 | 9/2013 |
| EP | 2600766 | B1 | 6/2017 |
| EP | 2812050 | B1 | 1/2019 |
| EP | 3213682 | B1 | 3/2020 |
| EP | 2950712 | B1 | 10/2020 |
| EP | 2391971 | B1 | 11/2021 |
| JP | 5723788 | B2 | 5/2015 |
| JP | 6005715 | B2 | 10/2016 |
| JP | 2016202974 | A | 12/2016 |
| WO | 2008009136 | A1 | 1/2008 |
| WO | 2011134083 | A1 | 11/2011 |
| WO | 2013025613 | A1 | 2/2013 |
| WO | 2013056231 | A1 | 4/2013 |
| WO | 2014150780 | A2 | 9/2014 |
| WO | 2014150961 | A1 | 9/2014 |

(56)                    References Cited

FOREIGN PATENT DOCUMENTS

| | | | |
|---|---|---|---|
| WO | 2018185729 | A1 | 10/2018 |
| WO | 2021011646 | A2 | 1/2021 |
| WO | 2021014211 | A1 | 1/2021 |

OTHER PUBLICATIONS

English language abstract for JP 5723788 B2 extracted from espacenet. com database on Aug. 10, 2022, 2 pages.

English language abstract for JP 6005715 B2 extracted from espacenet. com database on Aug. 10, 2022, 2 pages.

He, PhD, He et al., "Test of Vertical Scan Mode in 3-D Imaging of Residual Limbs Using Ultrasound", https://www.rehab.research.va. gov/jour/99/36/2/he.htm, Journal of Rehabilitation Research and Development, vol. 36, No. 2, Apr. 1999, 10 pages.

U.S. Appl. No. 63/390,058, filed Jul. 18, 2022.

* cited by examiner

TRACKING APPARATUS FOR TRACKING A PATIENT LIMB

CROSS-REFERENCE TO RELATED APPLICATIONS

The present application claims priority to and all the benefits of U.S. Provisional Patent Application No. 63/231,308, filed on Aug. 10, 2021, the contents of which are hereby incorporated by reference in their entirety.

TECHNICAL FIELD

The present disclosure relates generally to a tracking apparatus configured to couple to a patient limb to track the patient limb.

BACKGROUND

The use of surgical navigation systems for assisting surgeons during surgery is quite common. Such systems are used to track the movement of bony structures to determine a location of the bony structure, and whether it has moved. Typical surgical navigation systems require invasively implanting trackers in the bone of the patient. Invasive implantation of trackers requires additional surgical steps, such as planning the location of the tracker, performing implantation, and performing manual bone registration using a pointer. Additionally, invasive implantation of trackers can potentially cause additional trauma to the patient. Furthermore, to increase accuracy of tracking, conventional systems require a tracking array extending from the bone. Such tracking arrays can reduce visibility of the surgical site and potentially interfere with the surgeon or surgical components of tools in the workspace. Conventional trackers additionally are susceptible to becoming dislodged or inadvertently moved, which in turn can compromise tracking accuracy. Multiple trackers are sometimes attached to the bone to increase tracking accuracy but doing so only amplifies the aforementioned challenges. There is a need in the art for systems and methods to address at least these challenges.

SUMMARY

This Summary introduces a selection of concepts in a simplified form that are further described in the Detailed Description below. This Summary is not intended to limit the scope of the claimed subject matter nor identify key features or essential features of the claimed subject matter.

According to a first aspect, a tracking apparatus for tracking a bone of a patient limb is provided. The tracking apparatus includes a body configured to couple to the patient limb, the body including first and second arms each including an exterior surface, an opposing interior surface, and opposing sides connecting the exterior and interior surfaces. The tracking apparatus also includes a wing portion extending from at least one of the sides of at least one of the first and second arms, the wing portion sharing the interior surface of the at least one first and second arm. The tracking apparatus also includes one or more ultrasonic sensors coupled to the interior surface of the body and the interior surface of wing portion, the one or more ultrasonic sensor being configured to transmit ultrasonic waves to and receive ultrasonic waves from the bone. The tracking apparatus also includes one or more trackable elements coupled to the body and the wing portion.

According to a second aspect, a tracking system for tracking a bone of a patient limb is provided. The tracking system includes a tracking apparatus, which includes a body and a wing portion extending from the body. The tracking apparatus includes one or more ultrasonic sensors coupled to the wing portion, the one or more ultrasonic sensor being configured to transmit ultrasonic waves to and receive ultrasonic waves from the bone. The tracking apparatus also includes one or more trackable elements coupled to the wing portion. The tracking system also includes a localizer configured to sense one or more of the trackable elements of the tracking apparatus and one or more controllers configured to determine a position of the bone relative to one or more of the trackable elements and in a coordinate system of the tracking apparatus based on the ultrasonic waves received by the one or more ultrasonic sensors, a position of one or more of the trackable elements in a coordinate system of the localizer based on the sensing of the one or more trackable elements by the localizer, and a position of the bone in a coordinate system of the localizer.

According to a third aspect, a robotic surgical system is provided. The robotic surgical system includes a manipulator including a robotic arm formed of a plurality of links and joints, an end effector coupled to the robotic arm and comprising an energy applicator, and a tracker coupled to one or more of the robotic arm and the end effector. The robotic surgical system also includes a tracking apparatus for tracking a bone of a patient limb, which includes a body and a wing portion extending from the body. The tracking apparatus includes one or more ultrasonic sensors coupled to the wing portion, the one or more ultrasonic sensor being configured to transmit ultrasonic waves to and receive ultrasonic waves from the bone. The tracking apparatus also includes one or more trackable elements coupled to the wing portion. The robotic surgical system also includes a localizer configured to sense one or more of the trackable elements of the tracking apparatus and one or more controllers configured to determine a position of the bone in a coordinate system of the localizer and a position of the energy applicator relative to the bone.

According to a fourth aspect, a tracking apparatus is provided for tracking a patient limb, the tracking apparatus comprising: a body configured to couple to the patient limb and comprising first and second arms each including an exterior surface, an opposing interior surface, and opposing sides connecting the exterior and interior surfaces; a wing portion extending from at least one of the sides of at least one of the first and second arms and the wing portion sharing the interior surface of the at least one first and second arm; one or more ultrasonic sensors coupled to the interior surface of the body and the interior surface of the wing portion and being configured to transmit ultrasonic waves to and receive ultrasonic waves from the patient limb; and one or more trackable elements coupled to the body and the wing portion.

According to a fifth aspect, a tracking apparatus having an ornamental design specifically shown in FIGS. 3-5 is provided.

According to a sixth aspect, a tracking apparatus for tracking a patient limb is provided. The tracking apparatus includes a body configured to at least partially wrap around the patient limb, the body including an exterior surface, an opposing interior surface, and opposing sides connecting the exterior and interior surfaces. The tracking apparatus also includes a wing portion extending from at least one of the sides of the body, the wing portion sharing the interior surface of the body. The tracking apparatus also includes one or more ultrasonic sensors coupled to the interior surface of the body and the interior surface of the wing portion, the one or more ultrasonic sensor being configured to transmit ultrasonic waves to and receive ultrasonic waves from the patient limb. The tracking apparatus also includes one or more trackable elements coupled to the body.

According to a seventh aspect, a tracking apparatus for tracking a patient limb is provided. The tracking apparatus comprising: a body configured to at least partially wrap around the patient limb; a wing portion integrally extending from the body; one or more ultrasonic sensors coupled to the body and the wing portion and being configured to transmit ultrasonic waves to and receive ultrasonic waves from the patient limb; and one or more trackable elements coupled to the body and the wing portion.

Any of the above aspects can be utilized individually, or in combination.

In one implementation, a space is defined between the interior surfaces of the first and second arms. In one implementation, an axis is defined through the space in a direction extending between the opposing side surfaces of the at least one first and second arms. In one implementation, the wing portion extends along a direction parallel to the axis. In one implementation, the bone comprises a bone axis. In one implementation, the first and second arms are configured to at least partially surround the bone. In one implementation, the axis along which the wing portion extends is configured to be parallel, or substantially parallel with the bone axis. In one implementation, each side has a side surface length. In one implementation, the wing portion has a wing portion length. In one implementation, the wing portion length is less than the side surface length. In one implementation, the at least one first and second arms and the wing portion each include an axial length defined along a direction of the axis. In one implementation, the axial length of the wing portion is greater than or substantially equal to the axial length of the at least one first and second arms.

In one implementation, the one or more trackable elements includes one or more of an optical trackable element configured to be sensed by an optical localizer, a radio frequency (RF) trackable element configured to be sensed by an RF localizer, an electromagnetic (EM) trackable element configured to be sensed by an EM localizer, and a pattern or feature configured to be sensed by a machine-vision camera localizer.

In one implementation, each of the first and second arms and the wing portion has an arcuate configuration.

In one implementation, the first and second arms are spaced apart from one another and are rigid. In one implementation, a hinge connects the first arm and the second arm such that the first arm and the second arm are rotatably moveable relative to one another relative to the hinge. In one implementation, the hinge includes a sensor configured to sense a relationship between the first and second arms. In one implementation, the tracking apparatus comprises one or more controllers configured to determine a relationship between the one or more of the ultrasonic sensors of the first arm and the one or more of the ultrasonic sensors of the second arm.

In one implementation, the one or more controllers are configured to calibrate the one or more ultrasonic sensors based on the relationship between the first and second arms.

In one implementation, the body is flexible to wrap around the patient limb. In one implementation, the first and second arms are integrally connected and are flexible such that the body moves between a closed position and an open position in response to flexing of one or more of the first and second arms. In one implementation, the first and second arms are spaced apart from one another and are flexible and a hinge connects the first arm and the second arm such that the first arm and the second arm are rotatably moveable relative to one another relative to the hinge.

In one implementation, the one or more trackable elements are coupled to the exterior surface of one or more of the first and second arms and coupled to the exterior surface of the wing portion.

In one implementation, the wing portion is further defined as a first wing portion. In one implementation, the tracking apparatus comprises a second wing portion extending from the body at a location separated from the first wing portion and the second wing portion sharing the interior surface of at least one of the first and second arm. In one implementation, one or more of the ultrasonic sensors is coupled to the interior surface of the second wing portion. In one implementation, one or more of the trackable elements is coupled to the exterior surface of the second wing portion.

In one implementation, the body includes a first distal end, an opposing second distal end, and a midpoint between the first and the second distal ends. In one implementation, the first wing portion is located between the first distal end and the midpoint of the body. In one implementation, the second wing portion is located between the midpoint and the second distal end of the body. In one implementation, the first distal end and the second distal end of the body are spaced from one another to define an opening configured to receive the patient limb.

In one implementation, the wing portion shares the exterior surface of the at least one first and second arm. In other implementations, the wing portion may extend entirely or partially from the exterior surface. In other implementations, the wing portion may extend entirely or partially from the interior surface.

In one implementation, the tracking apparatus comprises a cushion coupled to the interior surface of the first and second arms and the interior surface of the wing portion. In one implementation, the cushion contacts the patient limb. In one implementation, the tracking apparatus comprises a fluid control unit coupled to the cushion and configured to provide fluid to the cushion. In one implementation, the tracking apparatus comprises a controller configured to determine an integrity of contact between the tracking apparatus and the patient limb based on the ultrasonic waves received by the one or more ultrasonic sensors. In one implementation, the controller is configured to adjust the one or more ultrasonic sensors in response to determining the integrity of contact. In one implementation, the tracking apparatus comprises a cushion coupled to the interior surface of the first and second arms and the interior surface of the wing portion. In one implementation, the cushion contacts the patient limb. In one implementation, a fluid control unit coupled to the cushion and configured to provide fluid to the cushion. In one implementation, the controller is configured to adjust the fluid control unit in response to determining the integrity of contact.

In one implementation, the tracking apparatus comprises a light emitter configured to emit light to the patient limb, an optical sensor configured to sense light reflected from the patient limb, and a controller coupled to the optical sensor and configured to determine an integrity of contact between the tracking apparatus and the patient limb based on the light sensed by the optical sensor.

In one implementation, the tracking apparatus comprises a controller coupled to the one or more ultrasonic sensors and being configured to determine a shape of the bone based on the ultrasonic waves received by the one or more ultrasonic sensors.

In one implementation, the tracking apparatus comprises a non-transitory memory coupled to the controller, the non-transitory memory configured to store the shape of the bone and the controller configured to determine a position of the bone relative to the one or more trackable elements in a coordinate system of the tracking apparatus based on the shape of the bone. In one implementation, the one or more controllers are configured to determine a shape of the bone based on the ultrasonic waves received by the one or more ultrasonic sensors.

In one implementation, the tracking apparatus comprises a display configured to display the position of the bone in the coordinate system of the localizer and the shape of the bone. In one implementation, the tracking apparatus comprises a controller of the one or more controllers. In one implementation, the one or more controllers comprises a controller remotely coupled to the tracking apparatus.

In one implementation, the tracking apparatus is further defined as a first tracking apparatus for a femur of a patient such that the body of the first tracking apparatus is configured to couple to the femur of the patient. In one implementation, the tracking system comprises a second tracking apparatus for a tibia of the patient such that the body of the second tracking apparatus is configured to couple to the tibia of the patient.

In one implementation, the hinge or hinges of the tracking apparatus may comprise motors for moving a first and/or second arms between an open and/or closed position.

Any of the above implementations can be combined in part, or in whole, with any of the aspects.

DESCRIPTION OF THE DRAWINGS

Advantages of the present disclosure will be readily appreciated as the same becomes better understood by reference to the following detailed description when considered in connection with the accompanying drawings.

DETAILED DESCRIPTION

I. Overview of Tracking System

Figure 1:
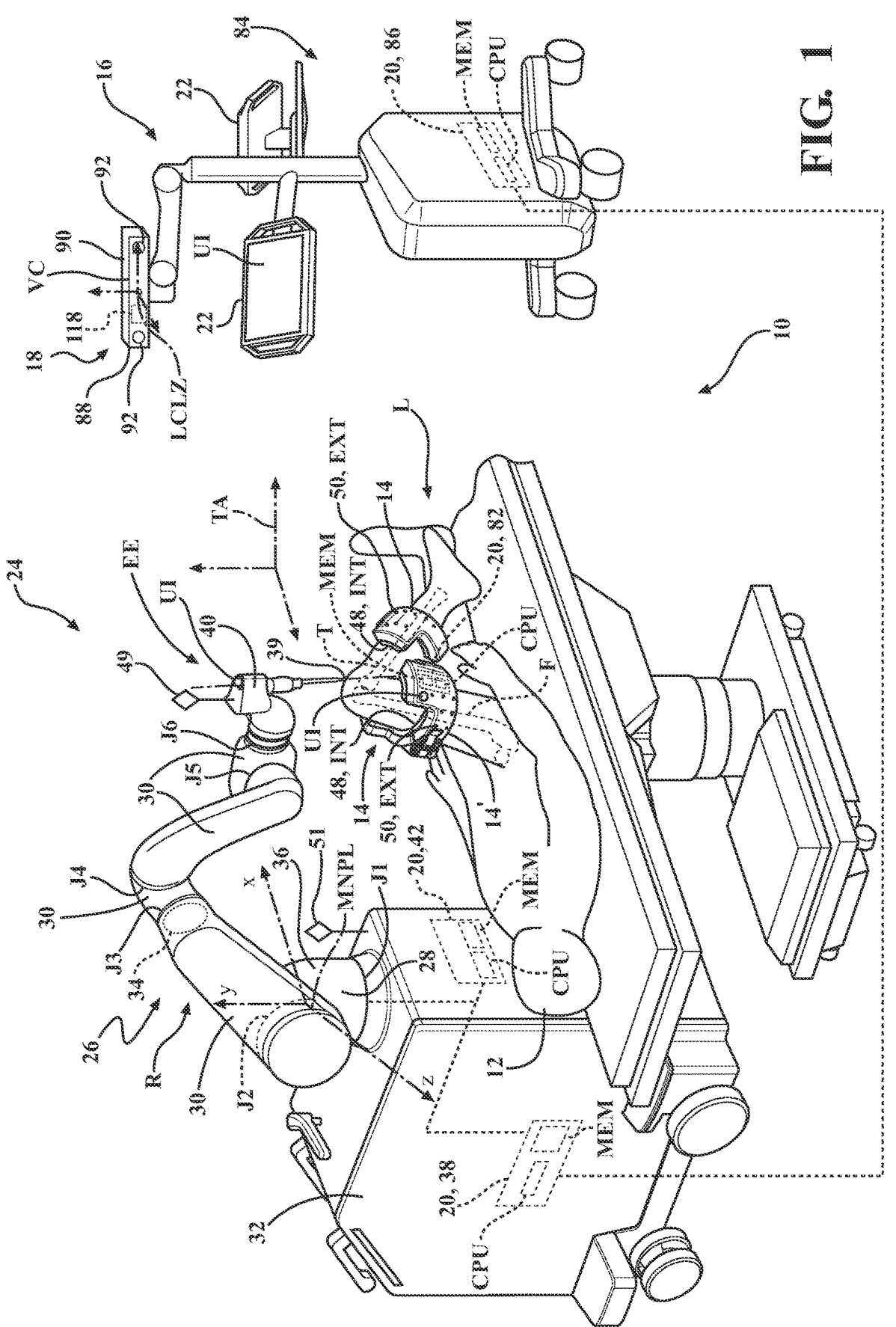
FIG. 1 is a perspective view of a tracking system and a robotic surgical system according to one example.

Referring to FIG. 1, a tracking system 10 is illustrated. The tracking system 10 is useful for non-invasively tracking and/or assessing a surgical site or an anatomical volume of a patient 12, such as bone or soft tissue. For example, in the instance of FIG. 1, the tracking system 10 tracks a femur F and/or a tibia T of the patient 12. Other bones, such as the humerus, pelvis, skull, and spine are contemplated.

As shown in FIG. 1, the tracking system 10 may include a tracking apparatus 14 which couples to the patient 12, specifically, a patient limb L, and tracks a bone of the patient limb L. In FIG. 1, the tracking system 10 includes a first tracking apparatus 14' for tracking the femur F and a second tracking apparatus 14" for tracking the tibia T.

The tracking apparatus 14 includes one or more ultrasonic sensors 48 coupled to an interior surface INT of the tracking apparatus 14. The ultrasonic sensors 48 are configured to transmit ultrasonic waves to and receive ultrasonic waves from the bone of the patient. Furthermore, the tracking apparatus 14 includes one or more trackable elements 50, which may be sensed by a localizer of the tracking system 10. In FIG. 1, the trackable elements 50 are shown as being coupled to an exterior surface EXT of the tracking apparatus 14.

The tracking system 10 may also include a navigation system 16, which may include a navigation localizer 18. The navigation localizer 18 may be configured to sense elements of the tracking system 10. For example, the navigation localizer 18 may be configured to sense the trackable elements 50 of the tracking apparatus 14, a tool tracker 49 attached to the tool 40, and/or a manipulator tracker 51 attached to the manipulator 26.

The tracking system 10 also includes one or more controllers 20. The one or more controllers 20 may be configured to determine a state of the bone of the patient 12 in a (navigation) localizer coordinate system LCLZ. As used herein, the state of an object includes, but is not limited to, data that defines a shape, surface contour, position, and/or an orientation of an object or equivalents/derivatives thereof. Additionally, the state may include linear velocity data, angular velocity data, acceleration, and the like.

For example, the one or more controllers 20 may be configured to determine a position of the bone of the patient 12 in the localizer coordinate system LCLZ and/or a shape of the bone of the patient 12. In an instance where the one or more controllers 20 determines a position of the bone of the patient 12, it may be stated that the one or more controllers 20 transform a state of the bone of the patient 12 from the tracking apparatus coordinate system TA to the localizer coordinate system LCLZ. Specifically, the one or more controllers 20 perform a first transform by determining a position of the bone of the patient 12 relative to one or more of the trackable elements 50 and in the tracking apparatus coordinate system TA based on ultrasonic waves received by the one or more ultrasonic sensors 48. The one or more controllers 20 may then perform a second transform by determining a position of the one or more trackable elements 50 in the localizer coordinate system LCLZ based on a sensing of the one or more trackable elements 50 by the localizer 18. The one or more controllers 20 may then combine the first and second transforms to determine the position of the bone in the localizer coordinate system LCLZ based on the position of the bone of the patient 12 in the tracking apparatus coordinate system TA (the first transform) and based on the position of the one or more trackable elements 50 in the localizer coordinate system LCLZ (the second transform).

The tracking system 10 may also include a display. For example, in the instance of FIG. 1, the tracking system 10 includes displays 22 of the navigation system 16. The displays 22 may be configured to display a state of the bone of the patient 12. In the instance of FIG. 1, the displays 22 may be configured to display data corresponding to a position of the femur F, as well as a shape of the femur F.

A. Example Robotic System

Figure 2:
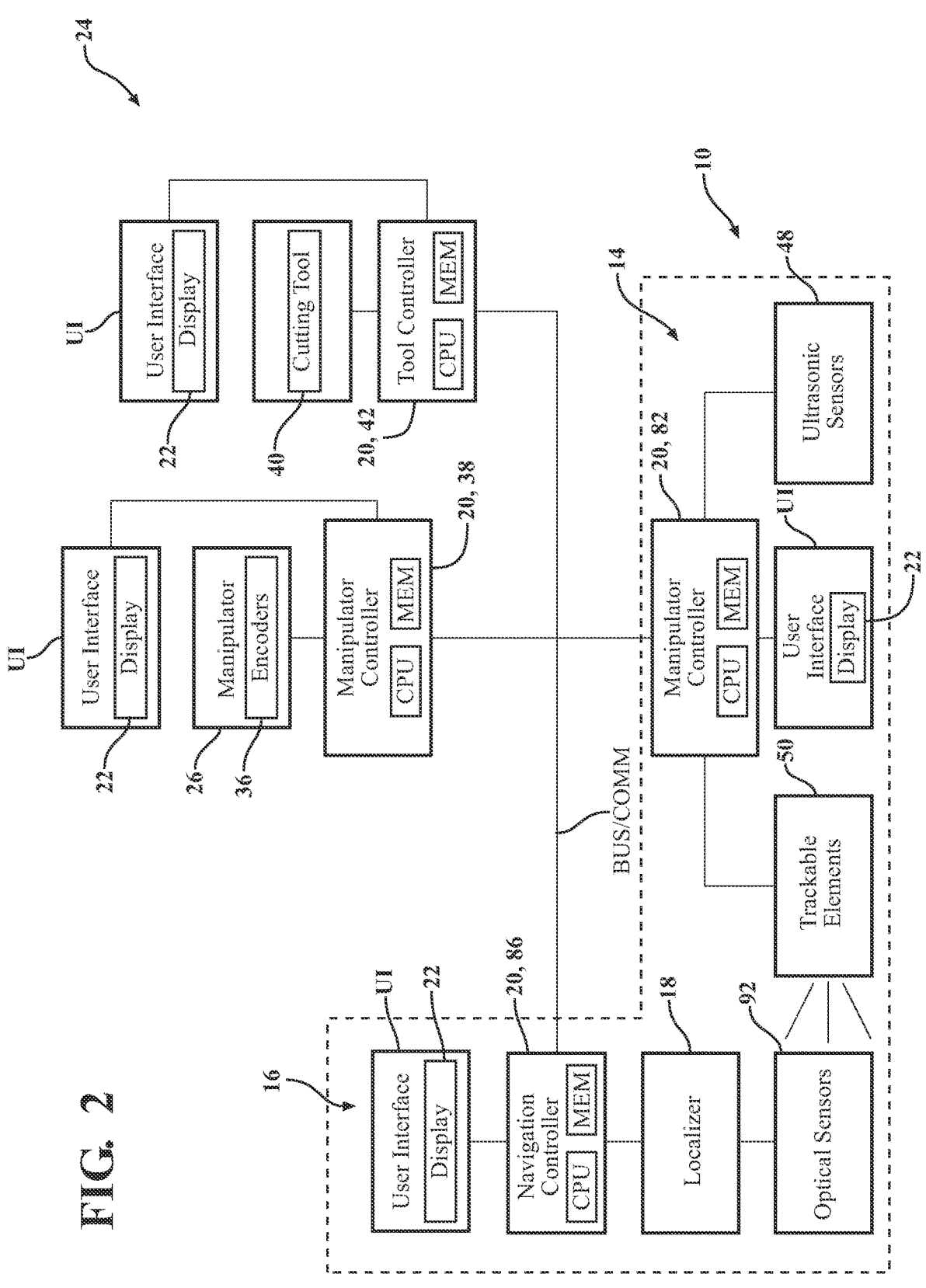
FIG. 2 is a block diagram of the tracking system and the robotic surgical system, according to one example.

As shown in FIG. 2, the tracking system 10 may be a part of a robotic surgical system 24, the tracking system 10 being delineated from the rest of the robotic surgical system 24 using a dashed-line box. The robotic surgical system 24 may be configured to carry out the surgical procedure based on the state of the bone as determined by the one or more controllers 20 of the tracking system 10. However, in some instances, the tracking system 10 may be independent of the robotic surgical system 24. In such instances, a surgeon may carry out a surgical procedure while referencing the position or shape of the bone, as displayed by the display 22 or as notified by the tracking system 10.

The robotic surgical system 24 may be configured to treat the surgical site or the anatomical volume of a patient 12A. In FIG. 1, the robotic surgical system 24 is shown performing a surgical procedure on the patient 12. The surgical procedure may involve tissue removal or other forms of treatment. Treatment may include cutting, coagulating, lesioning the tissue, other in-situ tissue treatments, or the like. As an example, the surgical procedure may involve partial or total knee replacement surgery. In some examples, the robotic surgical system 24 may be designed to cut away material to be replaced by surgical implants, such as knee implants, including unicompartmental, bicompartmental, multicompartmental, or total knee implants. Some of these types of implants are shown in U.S. Patent Application Publication No. 2012/0330429, entitled "Prosthetic Implant and Method of Implantation," the disclosure of which is hereby incorporated by reference. The robotic surgical system 24 and techniques disclosed herein may be used to perform other procedures, surgical or non-surgical, or may be used in industrial applications or other applications where robotic systems are utilized.

As shown in FIG. 1, the robotic surgical system 24 may include a manipulator 26. The manipulator 26 has a base 28 and a plurality of links 30. A manipulator cart 32 supports the manipulator 26 such that the manipulator 26 is fixed to the manipulator cart 32. The links 30 collectively form one or more robotic arms R of the manipulator 26. The manipulator 26 may have a serial arm configuration (as shown in FIG. 1), a parallel arm configuration, or any other suitable manipulator configuration. In other examples, more than one manipulator 26 may be utilized in a multiple arm configuration.

In the example shown in FIG. 1, the manipulator 26 comprises a plurality of joints J and a plurality of joint encoders 34 located at the joints J for determining position data of the joints J. For simplicity, only one joint encoder 34 is illustrated in FIG. 1, although other joint encoders 34 may be similarly illustrated. The manipulator 26 according to one example has six joints J1-J6 implementing at least six-degrees of freedom (DOF) for the manipulator 26. However, the manipulator 26 may have any number of degrees of freedom and may have any suitable number of joints J and may have redundant joints.

The manipulator 26 need not require joint encoders 34 but may alternatively, or additionally, utilize motor encoders present on motors 36 coupled to any number of joints J. Also, the manipulator 26 need not require rotary joints, but may alternatively, or additionally, utilize one or more prismatic or linear joints. Any suitable combination of joint types is contemplated.

As shown in FIG. 1, the base 28 of the manipulator 26 is a portion of the manipulator 26 that provides a fixed reference coordinate system for other components of the manipulator 26 or the robotic surgical system 24 in general. Generally, the origin of a manipulator coordinate system MNPL is defined at the fixed reference of the base 28. The base 28 may be defined with respect to any suitable portion of the manipulator 26, such as one or more of the links 30. Alternatively, or additionally, the base 28 may be defined with respect to the manipulator cart 32, such as where the manipulator 26 is physically attached to the manipulator cart 32. In one example, the base 28 is defined at an intersection of the axes of joints J1 and J2. Thus, although joints J1 and J2 are moving components in reality, the intersection of the axes of joints J1 and J2 can be a virtual fixed reference pose, which provides both a fixed position and orientation reference and which does not move relative to the manipulator 26 and/or manipulator cart 32. In other examples, the manipulator 26 can be a hand-held manipulator where the base 28 is a base portion of a tool (e.g., a portion held free hand by the user), and the tool tip is movable relative to the base portion. The base portion has a reference coordinate system that is tracked, e.g., via the manipulator tracker 51, and the tool tip has a tool tip coordinate system that is computed relative to the reference coordinate system (e.g., via motor and/or joint encoders and forward kinematic calculations). Movement of the tool tip can be controlled to follow the path since its pose relative to the path can be determined.

The manipulator 26 and/or manipulator cart 32 house a manipulator controller 38, or other type of control unit. The manipulator controller 38 may comprise one or more computers, or any other suitable form of controller that directs the motion of the manipulator 26. The manipulator controller 38 may have a central processing unit CPU and/or other processors, memory MEM, and storage (not shown). The manipulator controller 38 is loaded with software as described below. The processors could include one or more processors to control operation of the manipulator 26. The processors can be any type of microprocessor, multi-processor, and/or multi-core processing system. The manipulator controller 38 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any implementation to a single processor. The manipulator 26 may also comprise a user interface UI with one or more displays 22 (shown in FIG. 2) and/or input devices (e.g., push buttons, keyboard, mouse, microphone (voice-activation), gesture control devices, touchscreens, etc.).

As shown in FIG. 1, a tool 40 couples to the manipulator 26 and is movable relative to the base 28 to interact with the anatomy in certain modes. The tool 40 is a physical and surgical tool and is or forms part of an end effector EE supported by the manipulator 26 in certain embodiments. The end effector EE may include an energy applicator 39, e.g., a bur, a drill bit, a saw blade, an ultrasonic vibrating tip, or the like, designed to contact and remove the tissue of the patient 12 at the surgical site. The tool 40 may be grasped by the user. One possible arrangement of the manipulator 26 and the tool 40 is described in U.S. Pat. No. 9,119,655, entitled "Surgical Manipulator Capable of Controlling a Surgical Instrument in Multiple Modes," the disclosure of which is hereby incorporated by reference. The manipulator 26 and the tool 40 may be arranged in alternative configurations. The tool 40 can be like that shown in U.S. Patent Application Publication No. 2014/0276949, filed on Mar. 15, 2014, entitled "End Effector of a Surgical Robotic Manipulator," hereby incorporated by reference.

The tool 40 may comprise a tool controller 42 to control operation of the tool 40, such as to control power to the tool (e.g., to a rotary motor of the tool 40), control movement of the tool 40, control irrigation/aspiration of the tool 40, and/or the like. The tool controller 42, as shown in FIG. 2, may be in communication with the manipulator controller 38 or other components. The tool 40 may also comprise a user interface UI with one or more displays 22 (shown in FIG. 2) and/or input devices (e.g., push buttons, keyboard, mouse, microphone (voice-activation), gesture control devices, touchscreens, etc.). The manipulator controller 38 controls a state (position and/or orientation) of the tool 40 (e.g., the tool center point (TCP)) with respect to a coordinate system, such as the manipulator coordinate system MNPL. The manipulator controller 38 can control (linear or angular) velocity, acceleration, or other derivatives of motion of the tool 40.

The manipulator controller 38 and/or the tool controller 42 may control operation of the robotic surgical system 24 during a manual mode, which is described in U.S. Pat. No. 9,119,655, incorporated herein by reference in its entirety. During the manual mode, the user manually directs, and the manipulator 26 executes, movement of the tool 40 at the surgical site. The user physically contacts the tool 40 to apply external force and cause movement of the tool 40 in the manual mode. The manipulator controller 38 and/or the tool controller 42 may control operation of the robotic surgical system 24 during a semi-autonomous mode, which is described in U.S. Pat. No. 9,119,655, incorporated herein by reference in its entirety. During the semi-autonomous mode, the manipulator 26 moves the tool 40 along a milling path (e.g., the active joints J of the manipulator 26 operate to move the tool 40 without necessarily requiring external force/torque on the tool 40 from the user). In some embodiments, when the manipulator 26 operates in the semi-autonomous mode, the manipulator 26 is capable of moving the tool 40 free of user assistance. Free of user assistance may mean that a user does not physically contact the tool 40 to move the tool 40. Instead, the user may use some form of remote control to control starting and stopping of movement. For example, the user may hold down a button of the remote control to start movement of the tool 40 and release the button to stop movement of the tool 40.

B. Example Navigation System

As shown in FIGS. 1 and 2, the tracking system 10 may include a navigation system 16. The navigation system 16 may be configured to sense the trackable elements 50 for determining a state of the tracking apparatus 14 with respect to the (navigation) localizer coordinate system LCLZ. In other instances, the navigation system 16 may also be configured to sense other elements for determining a state of the manipulator 26 and/or the tool 40. For example, the navigation system 16 may track the tool tracker 49 for determining a state of the tool 40 and/or the manipulator tracker 51 for determining a state of the manipulator 26. The navigation system 16 may also be configured to directly track an anatomy of the patient 12, e.g., femur F and tibia T, without tracking the tracking apparatus 14. One example of the navigation system 16 is described in U.S. Pat. No. 9,008,757, filed on Sep. 26, 2013, entitled "Navigation System Including Optical and Non-Optical Sensors," hereby incorporated by reference.

As shown in FIG. 1, the navigation system 16 may include a cart assembly 84 that houses a navigation controller 86, and/or other types of control units. A navigation user interface UI may be in operative communication with the navigation controller 86. The navigation user interface may include one or more displays 22 (shown in FIG. 2). The navigation system 16 may be capable of displaying a graphical representation of the relative states of the tracked objects to the user using the one or more displays 22. The navigation user interface UI may further include one or more input devices to input information into the navigation controller 86 or otherwise to select/control certain aspects of the navigation controller 86. Such input devices may include interactive touchscreen displays. The input devices may include any one or more of push buttons, a keyboard, a mouse, a microphone (voice-activation), gesture control devices, and the like.

As previously stated, the navigation system 16 may also include the navigation localizer 18. In the instance of FIG. 1, the localizer 18 is an optical localizer and includes a camera unit 88. The camera unit 88 has an outer casing 90 that houses one or more optical sensors 92. The localizer 18 may further comprise a video camera VC and a localizer controller 120, as shown in FIG. 1. The localizer controller 120 may be configured to control components of the localizer 18, such as the optical sensors 92 and/or the video camera VC.

As shown in FIG. 2, the localizer 18 may be coupled to the navigation controller 86. As such, the localizer 18 of the navigation system 16 may sense the one or more trackable elements 50 of the tracking apparatus 14 and the navigation controller 86 may determine a state of the tracking apparatus 14 based on the sensing performed by the localizer 18. For example, the localizer 18 may perform known triangulation techniques to sense the trackable elements 50 and communicate tracking information of the trackable elements 50 with the navigation controller 86 such that the navigation controller 86 is able to determine the state of the tracking apparatus 14.

In some instances, the localizer 18 of the navigation system 16 may be configured to sense objects other than the trackable elements 50 of the tracking apparatus 14. For example, in instances where the tracking system 10 is a part of the robotic surgical system 24, the localizer 18 may also be configured to sense a trackable element attached to the manipulator 26, the tool 40, and/or the anatomy of the patient 12 and the navigation controller 86 may be configured to determine a state of the manipulator 26, the tool 40, and/or the anatomy of the patient 12. For example, the localizer 18 may sense the tool tracker 49 attached to the tool 40, the manipulator tracker 51 attached to the manipulator 26, and/or patient trackers coupled to the femur F and tibia T using known triangulation techniques. Furthermore, in such instances, the navigation controller 86 may be configured to communicate a state of the trackable elements 50 to the manipulator controller 38 via a wired bus, communication network, as shown in FIG. 2, via wireless communication, or otherwise.

The navigation system 16 may use any suitable configuration for tracking the manipulator 26, tool 40, and/or the patient 12, in addition to, or instead of, known triangulation techniques. For instance, the navigation system 16 and/or localizer 18 may be ultrasound-based. In such an instance, the navigation system 16 may comprise an ultrasound imaging device coupled to the navigation controller 86. The ultrasound imaging device may image any of the aforementioned objects, e.g., the tracking apparatus 14, the manipulator 26, the tool 40, and/or the patient 12, and generates state signals to the navigation controller 86 based on the ultrasound images. The ultrasound images may be 2-D, 3-D, or a combination of both. The navigation controller 86 may process the images in near real time to determine states of the objects. The ultrasound imaging device may have any suitable configuration and may be different than the camera unit 88 as shown in FIG. 1.

In other instances, the navigation system 16 may include an optical localizer, a radio frequency (RF) based localizer, an electromagnetically (EM) based localizer, and/or a machine-vision based localizer. In such instances, the navigation system 16 may be configured to sense a corresponding type of object. For example, the navigation system 16 may be configured to sense an optical trackable element, an RF sensor or emitter, an EM sensor or emitter, and/or an object including a pattern or feature detectable by a machine-vision camera localizer.

The navigation controller 86 may comprise one or more computers, or any other suitable form of controller. As shown in FIGS. 1 and 2, the navigation controller 86 may include a central processing unit CPU and/or other processors, memory MEM, and storage (not shown). The processors can be any type of processor, microprocessor, or multiprocessor system. The navigation controller 86 may be loaded with software. The software, for example, may convert signals received from the localizer 18 into data representative of a state of objects being tracked. The navigation controller 86 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any implementation to a single processor.

The navigation system 16 may have any other suitable components or structure not specifically recited herein. Furthermore, any of the techniques, methods, and/or components described above with respect to the navigation system 16 shown may be implemented or provided for any of the other examples of the navigation system 16 described herein. For example, the navigation system 16 may utilize solely inertial tracking or any combination of tracking techniques, and may additionally, or alternatively, comprise fiber optic-based tracking, machine-vision tracking, and the like.

C. Example Tracking Apparatus

Figure 3:
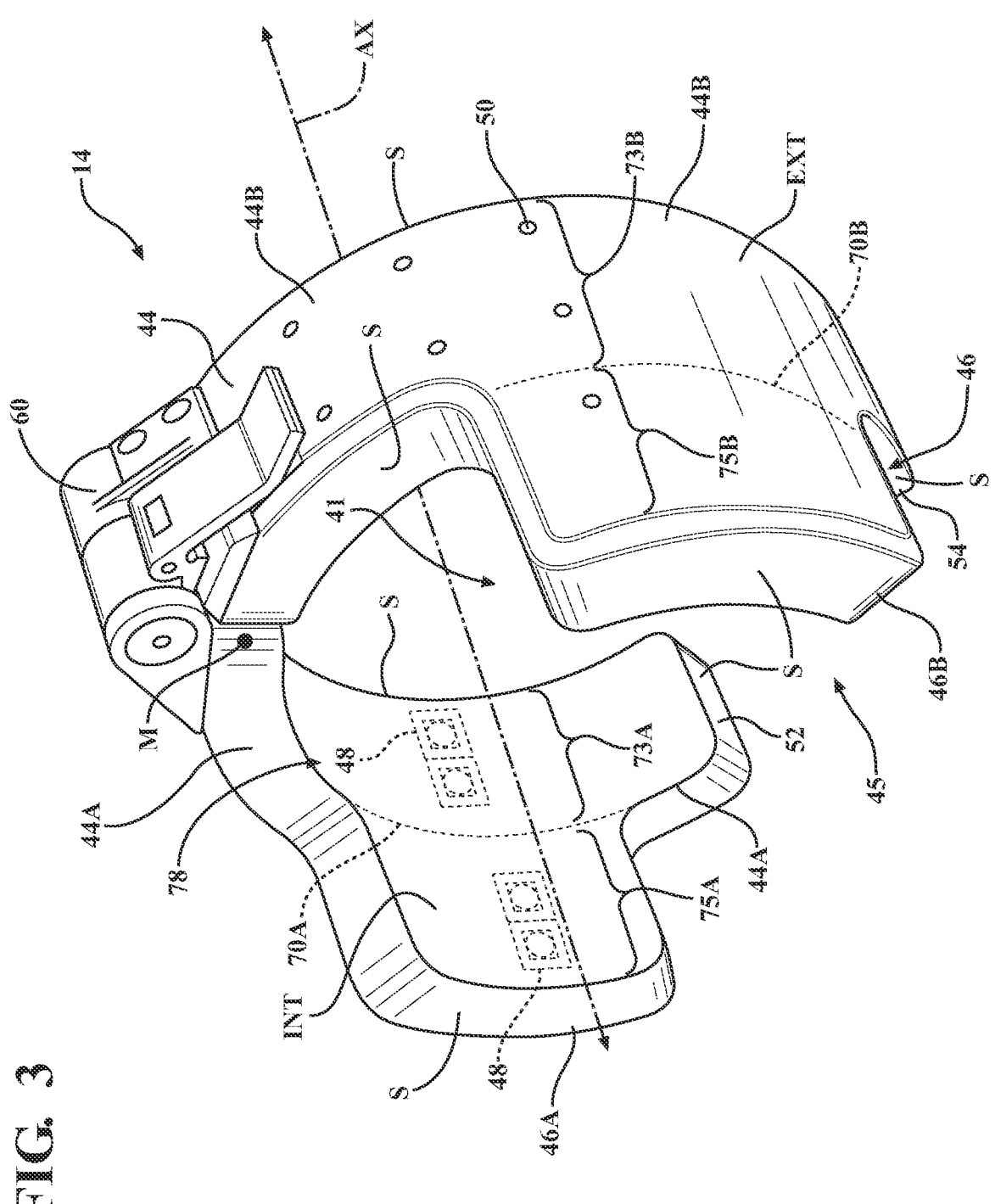
FIG. 3 is a perspective view of an implementation of the tracking apparatus of the tracking system, wherein the tracking apparatus has a rigid body with a hinged configuration.

One implementation of the tracking apparatus 14 of the tracking system 10 is shown in FIGS. 1 and 3. As shown in FIGS. 1 and 3, the tracking apparatus 14 includes a body 44, a wing portion 46, one or more ultrasonic sensors 48, and one or more trackable elements 50.

The body 44 is configured to couple to a patient limb L as shown in FIG. 1. As shown in FIG. 3, the body 44 may include a first arm 44A and a second arm 44B. Each of the first and second arms 44A, 44B include an exterior surface EXT, an opposing interior surface INT, and opposing sides S connecting the exterior and interior surfaces. The body 44 is configured to couple to the patient limb such that the first and second arms 44A, 44B are configured to at least partially surround the bone of the patient 12.

Figure 4:
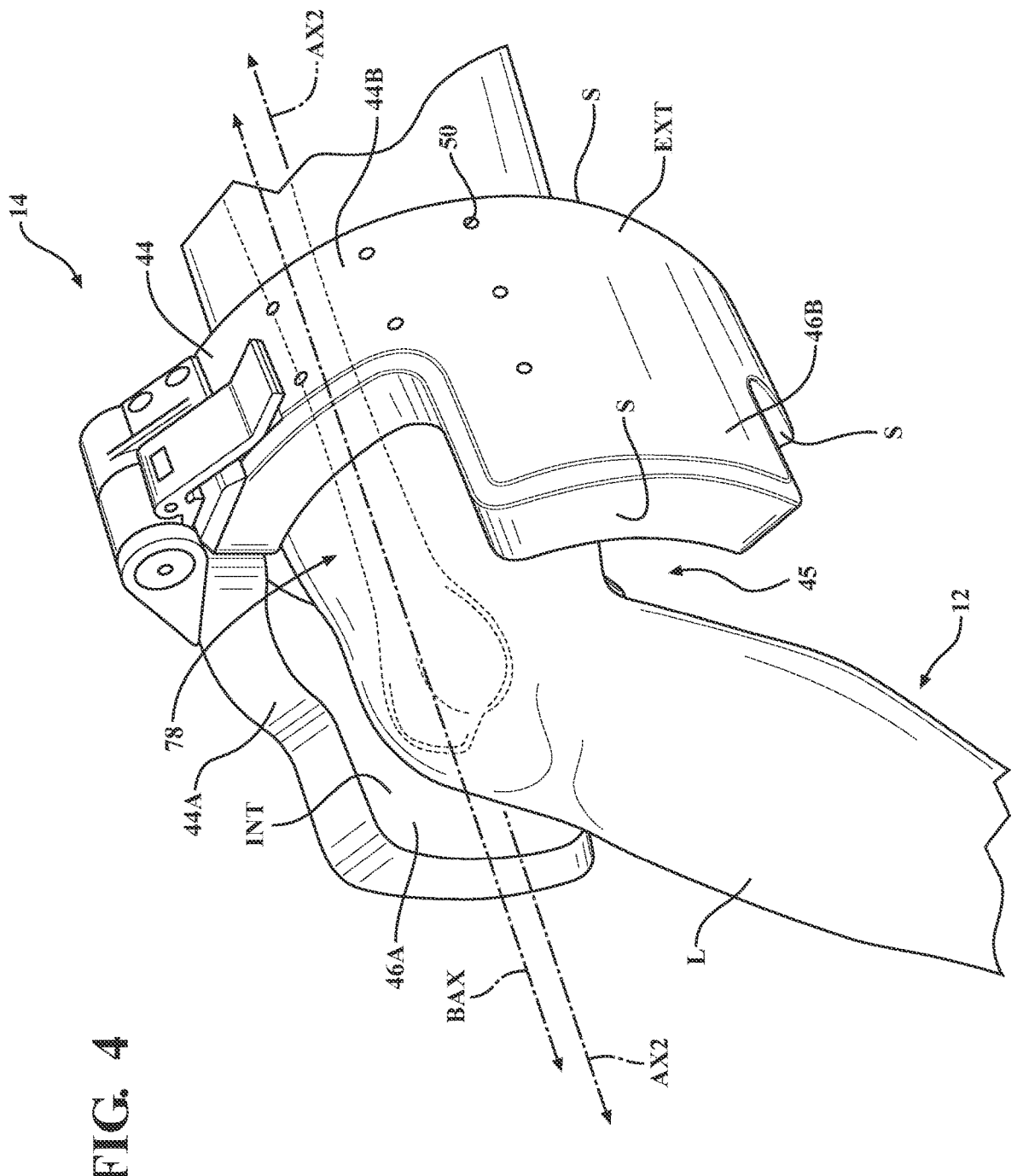
FIG. 4 is a perspective view of the tracking apparatus of the tracking system coupled to a patient limb.

Referring to FIG. 3, a space 41 may be defined between the interior surfaces INT of the first and second arms 44A, 44B. An axis AX may be defined through the space 41 in a direction extending between the opposing side surfaces S of the first and second arms 44A, 44B. As shown in FIG. 4, a bone of the patient limb L, represented as a femur F in FIG. 4, may include a bone axis BAX. The first and second arms 44A, 44B are configured to couple to the patient limb L such that the axis AX is parallel or substantially parallel with the bone axis BAX. It is not necessary that the axis AX be perfectly aligned with the bone axis BAX.

As shown in FIG. 3, the body 44 may include an opening 45. As shown, the body 44 includes a first distal end 52 and an opposing second distal end 54. The first distal end 52 and the second distal end 54 are spaced from one another to define the opening 45. The opening 45 may be configured to receive the patient limb L such that the body 44 may couple to the patient limb L, as shown in FIG. 4. The opening 45 is sized such that when the body 44 is closed, the tracking apparatus 14 should remain secured to the limb L. In other words, when the body 44 is closed, the opening 45 is sized to be narrower than a statistically below average sized patient limb such that the patient limb cannot escape the opening when the body 44 is closed. The opening 45 is also sized such that when the body 44 is fully open, the tracking apparatus 14 can secure to any size patient limb. In other words, when the body 44 is fully open, the opening 45 is sized to be wider than a statistically above average sized patient limb such that the patient limb can easily fit within the opening when the body 44 is open.

Figure 5:
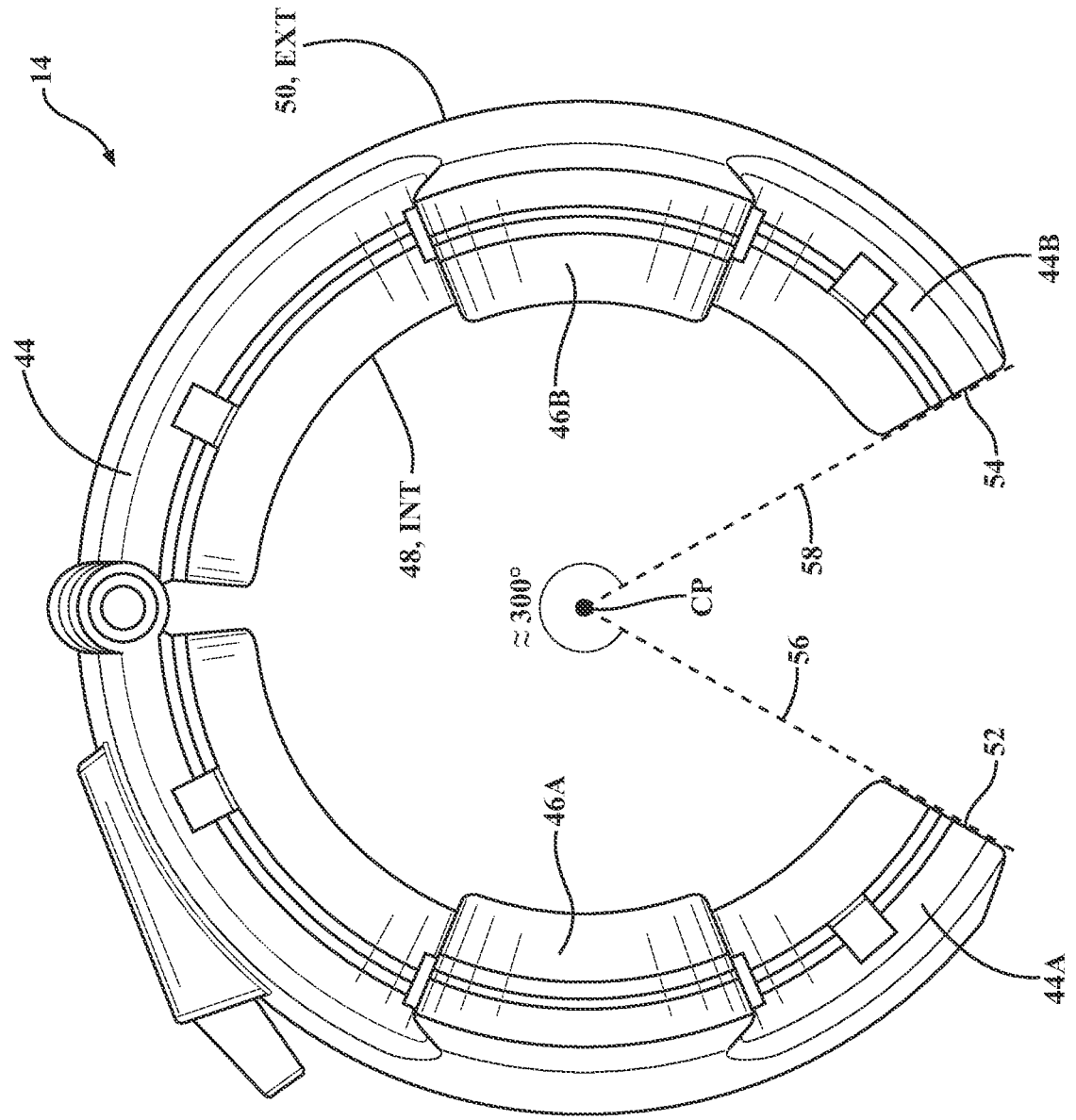
FIG. 5 is a side view of the tracking apparatus of the tracking system.

The first and second arms 44A, 44B may include an arcuate configuration. As shown in FIG. 5, the arcuate configuration of the first and second arms 44A, 44B may be substantially circular and curved about a center point CP of the tracking apparatus 14. Furthermore, the arcuate configuration of the first and second arms 44A, 44B may be defined between the first distal end 52 and the second distal end 54. In the instance of FIG. 5, the arcuate configuration of the body 44 is curved about the center point CP. Additionally, the tracking apparatus 14 is positioned such that an angle between a line 56 drawn from the center point CP to the first distal end 52 and a line 58 drawn from the center point CP to the second distal end 54 is approximately 300 degrees, as illustrated in FIG. 5. In other positions of the tracking apparatus 14 (e.g., an open or closed position to be explained herein), an angle between the line 56 and the line 58 may be any suitable degree. Additionally, in other instances, the arcuate configuration of the first and second arms 44A, 44B may be any suitable arc. For instance, the arcuate configuration of the first and second arms 44A, 44B may be substantially elliptical. Furthermore, it is not necessary to define the arcuate shape of the first and second arms 44A, 44B with respect to the center point CP. Other types of points or references may be defined within the limb L capturing region of the first and second arms 44A, 44B.

The tracking apparatus 14 may include any suitable number of bodies 44. In the instance of FIG. 3, the tracking apparatus 14 includes a single body 44. In other instances, the tracking apparatus 14 may include additionally bodies 44, which may be coupled to or integrally formed with one another.

Figures 6A, 6B:
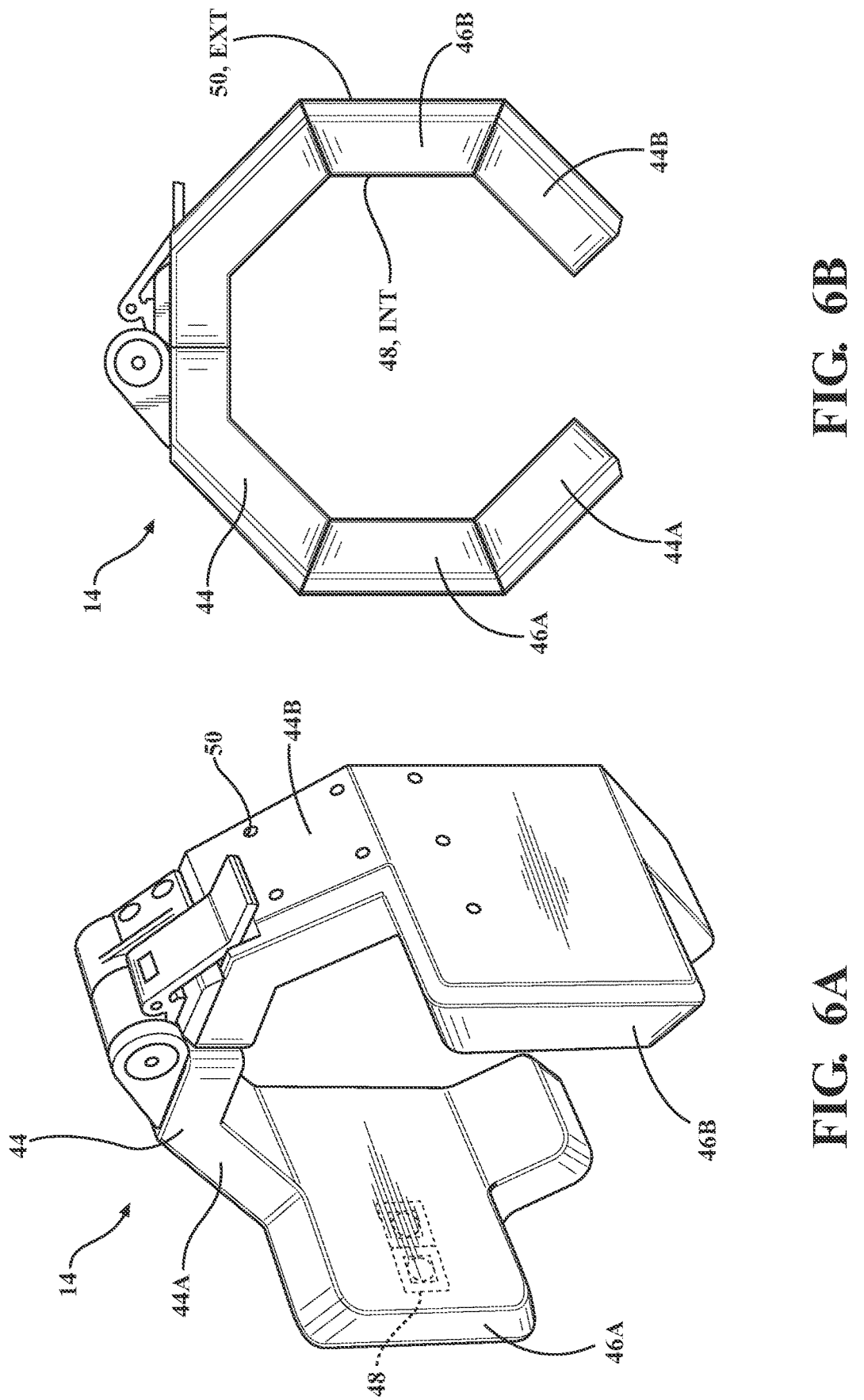
FIGS. 6A and 6B are a perspective view and a side view of another implementation of the tracking apparatus.

The body 44 may include any suitable shape and any suitable configuration. FIGS. 6A and 6B illustrate an alternative instance of the body 44 of the tracking apparatus 14 wherein the body 44 includes a polygonal configuration with several planar faces on the interior and exterior surfaces INT, EXT. In other instances, the body 44 may include any suitable polygonal configuration or combinations thereof.

As shown in FIG. 3, the first and second arms 44A, 44B may be spaced apart from one another and connected to one another by a hinge 60. The hinge 60 may connect the first and second arms 44A, 44B such that the first and second arms 44A, 44B are rotatably moveable relative to one another relative to the hinge 60.

Figures 8A, 8B:
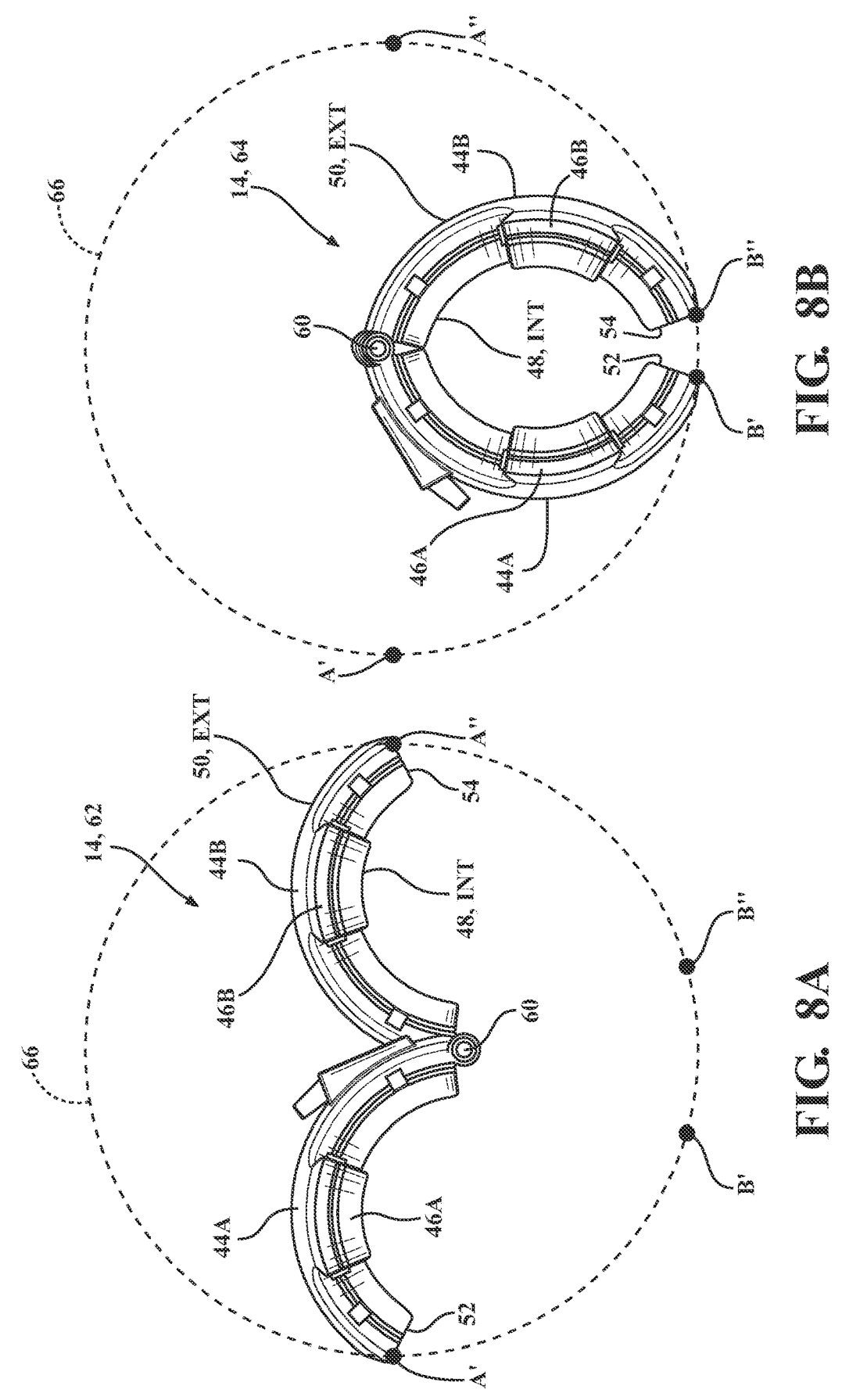
FIGS. 8A and 8B are side views of the tracking apparatus, wherein the tracking apparatus is positioned in an open position and a closed position.

Referring to FIGS. 8A and 8B, the first and second arms 44A, 44B rotate about the hinge 60 to position the tracking apparatus 14 in an open position 62 and a closed position 64 and any position therebetween. Specifically, in this implementation, the first and second arms 44A, 44B rotate about the hinge 60 along the circular path 66, to position the tracking apparatus 14 in the open position 62 and in the closed position 64. In the open position 62, as shown in FIG. 8A, the first distal end 52 is located at a point A' along the circular path 66 and the second distal end 54 is located at a point A" along the circular path 66. In the closed position 64, as shown in FIG. 8B, the first distal end 52 is located at a point B' along the circular path 66 and the second distal end 54 is located at a point B" along the circular path 66. In other instances, the first and second distal ends 52, 54 may be located at any suitable point along the circular path 66 during the open position 62 and during the closed position 64. In other examples, the path 66 along which the first and second distal ends 52, 54 follow may be other than circular. For example, the path 66 can be linear or follow other types of curved or irregular paths.

The body 44 may include any suitable material. In the examples shown including the hinge 60, the first and second arms 44A, 44B may be comprised of a rigid material. Alternatively, the body 44 may include a flexible material, such as a rubber, thin metallic material, polycarbonate, carbon fiber, plastic, or any suitable elastomeric material. In instances where the first and second arms 44A, 44B comprises a flexible material, the tracking apparatus 14 may include or omit the hinge 60. In instances where the tracking apparatus 14 omits the hinge 60, the first and second arms 44A, 44B may be integrally connected.

Figure 7A:
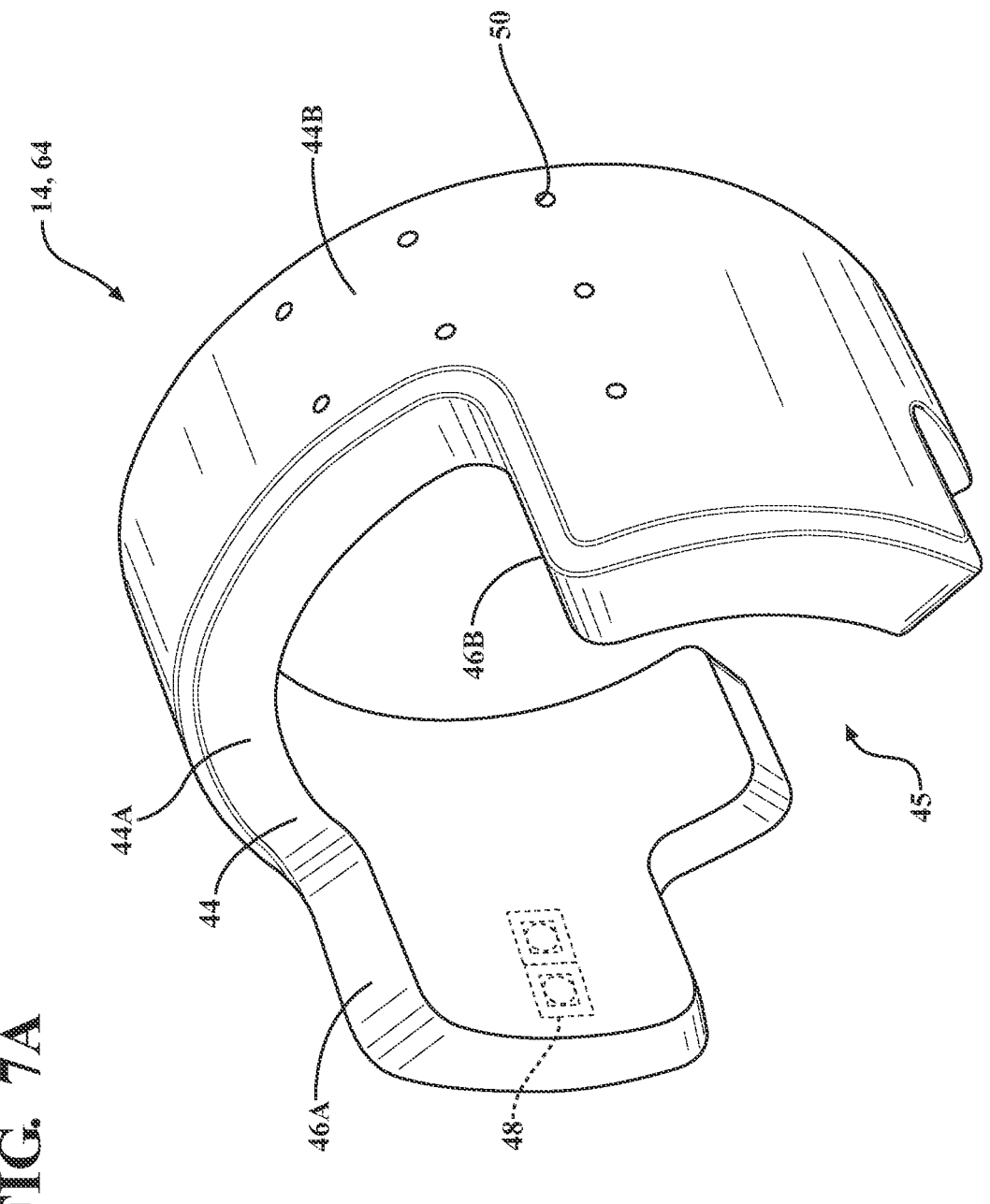
FIG. 7A is a perspective view of another implementation of the tracking apparatus, wherein the tracking apparatus has a flexible body, wherein the flexible body is shown at rest in a closed position.
Figure 7B:
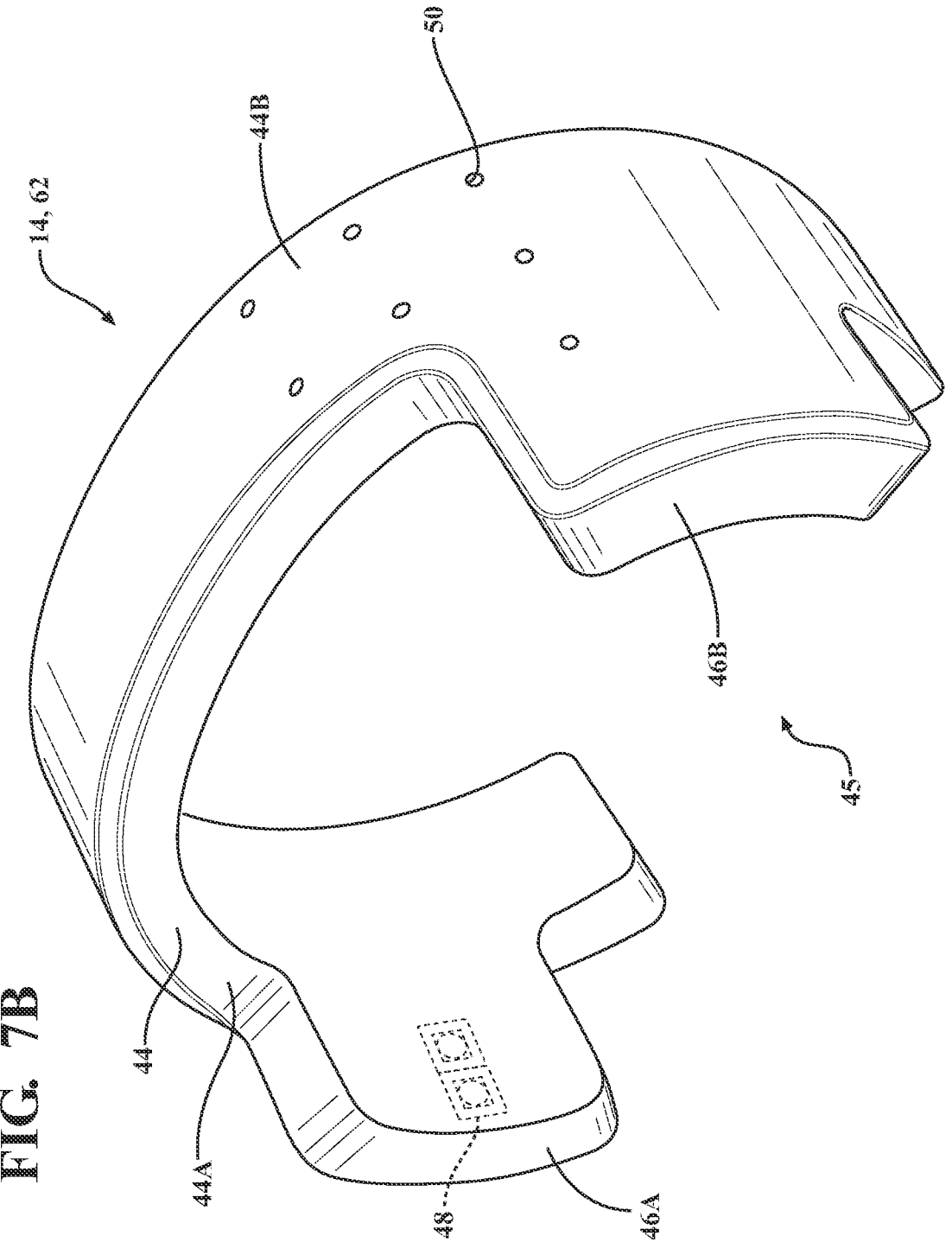
FIG. 7B is a perspective view of another implementation of the tracking apparatus, wherein the tracking apparatus has a flexible body, wherein the flexible body is shown flexed to an open position.

FIGS. 7A and 7B illustrates an instance where the first and second arms 44A, 44B comprise a flexible material, are integrally connected, and the tracking apparatus 14 omits the hinge 60. As shown, for flexible configurations, the body 44 may move between the closed position 64, shown in FIG. 7A, and the open position 62, shown in FIG. 7B, in response to flexing of one or more of the first and second arms 44A, 44B. In such instances, the body 44 may be biased towards the closed position 64 and moved towards the open position

62 in response to some external force flexing one or more of the first and second arms 44A, 44B. For example, the force can be applied by an operator pulling apart the first and second arms 44A, 44B during installation of the tracking apparatus 14 and/or can be applied by the patient limb L pressing against the body 44. Once installed onto the patient limb L, the flexible body 44 biases towards the closed position 64 thereby securing the body 44 to the patient limb L. The body 44 can include an adjustment mechanism, such as a mechanical separator between first and second arms 44A, 44B.

In some instances, the body 44 of the tracking apparatus 14 may comprise modular or multiple linkages that pivotally connected to one another, such as those described in PCT Pat. Pub. No. WO 2021/014211, which is hereby incorporated by reference in its entirety. For example, the first and/or second arms 44A, 44B of could be formed of such linkages. Alternatively, any suitable number of linkages may be added to a distal end 52, 54 of the body 44. Accordingly, the tracking apparatus 14 may include any suitable number of hinges 60 coupled between any number of linkages. For example, the linkages may be coupled to the first distal end 52 and/or the second distal end 54 of the body 44 using a coupling mechanism (not shown) to accommodate a larger patient limb L. In one such instance, a plurality of linkages may be coupled to one another to form a series of linkages, as described in PCT Pat. Pub. No. WO 2021/014211, and the series of linkages may be coupled to the body 44. As with the first and/or second arms 44A, 44B, the linkages similarly comprise ultrasonic sensors 48 and trackable elements 50. At least one of the linkages comprises a wing portion 46. The linkages, when connected, may be "plug-and-play" such that the tracking apparatus 14 may operate the ultrasonic sensors 48 and trackable elements 50 of the connected linkages, determine the number of connected linkages, and determine a relative position of the connected linkages.

In some instances, the tracking apparatus 14 may include a sensor configured to sense a relationship between the first and second arms 44A, 44B. The relationship between the first and second arms 44A, 44B may be a distance between the first and second arms 44A, 44B, and/or a position, a relative velocity, a relative acceleration, or an angle and/or orientation of one of the first and/or second arms 44A, 44B relative to the other of the first and/or second arms 44A, 44B, and/or equivalents/derivatives thereof.

In an instance when the sensor senses a distance between the first and second arms 44A, the sensor may include a distance measuring feature. For example, the sensor may include an ultrasonic sensor, an infrared (IR) sensor, a laser distance (LIDAR) sensor, a time-of-flight sensor, or other known features for measuring distance. The sensor may also sense a position, a relative velocity, a relative acceleration, and/or an angle and/or orientation of one of the first and/or second arms 44A, 44B relative to the other of the first and/or second arms 44A, 44B using an above component.

In an instance when the sensor senses a position of one of the first and/or second arms 44A, 44B relative to the other of the first and/or second arms 44A, 44B, the sensor may include a position measuring feature. For example, the sensor may include joint encoders, inductive sensors, capacitive sensors, transducers, or other known features for measuring position. The sensor may also sense a distance between the first and second arms 44A, and/or a relative velocity, a relative acceleration, or an angle and/or orientation of one of the first and/or second arms 44A, 44B relative to the other of the first and/or second arms 44A, 44B using an above component.

In an instance where the sensor senses an angle and/or orientation of one of the first and/or second arms 44A, 44B relative to the other of the first and/or second arms 44A, 44B, the sensor may be disposed within the hinge 60. Such a sensor may include transducers, piezoelectric elements in or connected to a spring of the hinge 60, servo motors as electromechanical angular biasing elements, or other known features for measuring an angle or orientation. In instances where the tracking apparatus 14 does not include the hinge 60 and the body 44 comprises flexible material, the sensor may include a stress/strain measuring feature for sensing a stress and/or strain on the flexible body 44 to sense an angle and/or orientation of one of the first and/or second arms 44A, 44B relative to the other of the first and/or second arms 44A, 44B. The stress/strain measuring feature may include a strain gauge, a load cell, a force sensor, or other known features for measuring stress or strain. The sensor may also sense a distance between the first and second arms 44A, and/or a position, a relative velocity, a relative acceleration, or an angle/orientation of one of the first and/or second arms 44A, 44B relative to the other of the first and/or second arms 44A, 44B using an above component.

The sensor configured to sense the relationship between the first and second arms 44A, 44B may be located in any suitable location of the tracking apparatus 14. For example, as previously stated, the sensor may be disposed within the hinge 60. In instances where the tracking apparatus 14 does not include the hinge 60, the sensor may be disposed within any other suitable component of the tracking apparatus 14, such as within the first and/or second arms 44A, 44B.

The one or more controllers 20 may be configured to determine the relationship between the first and second arms 44A, 44B based on the relationship between the first and second arms 44A, 44B sensed by the sensor. For example, the one or more controllers 20 may be configured to determine a relationship between the ultrasonic sensors 48 of the first and second arms 44A, 44B and a relationship between the trackable elements 50 of the first and second arms 44A, 44B based on the sensed relationship.

The one or more controllers 20 may be configured to determine a relationship between the ultrasonic sensors 48 of the first and second arms 44A, 44B based on the sensed relationship to calibrate the ultrasonic sensors 48 accordingly. For example, in some instances, the one or more controllers 20 may be configured to determine a position of the ultrasonic sensors 48 of the first arm 44A relative to a position of the ultrasonic sensors 48 of the second arm 44B based on the sensed relationship. The one or more controllers 20 may then calibrate the ultrasonic sensors 48 of the first and second arms 44A, 44B based on the relative position. This configuration of the one or more controllers 20 offers an advantage of the tracking system 10 as the one or more controllers 20 may determine the position of the bone in the tracking apparatus coordinate system TA with increased accuracy.

The one or more controllers 20 may be configured to determine a relationship between the trackable elements 50 of the first and second arms 44A, 44B based on the sensed relationship to confirm the state of the tracking apparatus 14 in the localizer coordinate system LCLZ. For example, as previously stated, the one or more controllers 20 may determine the state of the tracking apparatus 14 based on the localizer 18 sensing the trackable elements 50. Additionally, the one or more controllers 20 may determine the state of the tracking apparatus 14 based on determining the relationship between the trackable elements 50 of the first and second arms 44A, 44B based on the sensed relationship. The one or more controllers 20 may then confirm whether the state of the tracking apparatus 14 as determined based on sensing by the localizer 18 corresponds to the state of the tracking apparatus 14 as determined based on the sensed relationship. This configuration of the one or more controllers 20 offers an advantage of the tracking system 10 as the one or more controllers 20 may determine the state of the tracking apparatus 14 with greater robustness.

In some instances, the localizer 18 may be unable to sense a suitable number of the trackable elements 50 for determining a state of the tracking apparatus 14 in the localizer coordinate system LCLZ. In one such instance, the trackable elements 50 may be located on either the first arm 44A or the second arm 44B. In another such instance, only the trackable elements 50 of one of the first and second arms 44A, 44B may be able to be sensed by the localizer 18 (e.g., a barrier exists between the localizer 18 and one or more trackable elements 50). In such an instance, the one or more controllers 20 may still determine a state of the tracking apparatus 14 by determining a relationship between the first and second arms 44A, 44B based on the sensed relationship. For example, in an instance where the first arm 44A includes trackable elements 50 and the second arm 44B does not include trackable elements 50, the controller may determine a relationship between the first and second arms 44A, 44B based on the sensor sensing the relationship between the first and second arms 44A, 44B. The controller may then determine a state (e.g., a position) of the second arm 44B based on the localizer 18 sensing the trackable elements 50 of the first arm 44A and the determined relationship between the first and second arms 44A, 44B. This configuration of the one or more controllers 20 offers an advantage of the tracking system 10 as the one or more controllers may still determine the state of the tracking apparatus 14 in instances where the localizer 18 is unable to sense a suitable number of the trackable elements 50.

The one or more controllers 20 may determine the relationship between the first and second arms 44A, 44B based on relationship data stored in a memory of the one or more controllers 20. For example, the relationship data may be stored in a lookup table of the memory. The relationship data stored in a lookup table may associate a relationship between the ultrasonic sensor 48 of the first and second arms 44A, 44B based on the relationship sensed by the sensor. Additionally, the relationship data may associate a relationship between the trackable elements 50 of the first and second arms 44A, 44B based on the relationship sensed by the sensor. As such, the one or more controllers 20 may be configured to determine a relationship between the ultrasonic sensors 48 of the first and second arms 44A, 44B and a relationship between the trackable elements 50 of the first and second arms 44A, 44B based on the sensed relationship.

The tracking apparatus 14 may also include a first wing portion 46A and a second wing portion 46B. The first wing portion 46A is shown in FIG. 3 and delineated from the body 44 using a dashed line 70A. The second wing portion 46B is delineated from the body 44 using a dashed line 70B. As shown, the first wing portion 46A may extend from a side S of the first and/or second arm 44A, 44B along a direction parallel to the axis AX. As shown in FIG. 4, in instances when the tracking apparatus 14 is coupled to the patient limb, the first wing portion 46A may extend from the first and/or second arm 44A, 44B in a manner that is substantially parallel or parallel to the bone axis BAX. Referring to FIG. 3, the second wing portion 46B may also extend from the first and/or second arm 44A, 44B along the axis AX. As shown in FIG. 4, the second wing portion 46B may also extend from the first and/or second arm 44A, 44B in a manner substantially parallel to the bone axis BAX.

While the tracking apparatus 14 of FIG. 3 includes a two first and second wing portions 46A, 46B, in other instances, the tracking apparatus 14 may include any suitable number of wing portions. Said differently, the tracking apparatus 14 may include a greater or lesser number of wing portions than shown in FIG. 3. For example, the tracking apparatus 14 may include at least one wing portion extending from the first and/or second arm 44A, 44B. The tracking apparatus 14 is configured to operate with wing portion 46 so long as the tracking elements 50 of the one wing portion 46 can be detected by a localizer of the tracking system 10.

The first and second wing portions 46A, 46B may be integrally formed with the first and second arms 44A, 44B. A shown in FIG. 3, the wing portion 46A may share the exterior surface EXT and the interior surface INT of the first arm 44A. The wing portion 68B may share the exterior surface EXT and the interior surface INT of the second arm 44B. In other instances, at least one of the first and second wing portions 46A, 46B may be separated from one or more of the first and second arms 44A, 44B and/or coupled to the first and second arms 44A, 44B. Also shown in FIG. 3, the first and second wing portions 46A, 46B may share the arcuate configuration of the first and second arms 44A, 44B. In other instances, the first and second wing portions 46A, 46B and the first and second arms 44A, 44B may include differing configurations.

Referring to FIG. 3, a size of the first and second wing portions 46A, 46B with respect to the first and second arms 44A, 44B is shown. As shown, the first arm 44A includes an axial length 73A defined along a direction of the axis AX and the second arm 44B includes an axial length 73B defined along a direction of the axis AX. The first and second wing portions 46A, 46B include an axial length 75A, 75B, respectively, defined along the axis AX. As shown, the axial lengths 75A, 75B of the first and second wing portions 46A, 46B are greater than or substantially equal (+/−2 centimeters) to the axial lengths 73A, 73B of the first and second arms 44A, 44B. In some instances, the axial length 75A of the first wing portion 46A may be greater than or less than the axial length 75B of the second wing portion 46B. Furthermore, the axial lengths 73A, 73B, 75A, 75B may vary from the lengths shown in FIG. 3.

Figures 9A, 9B:
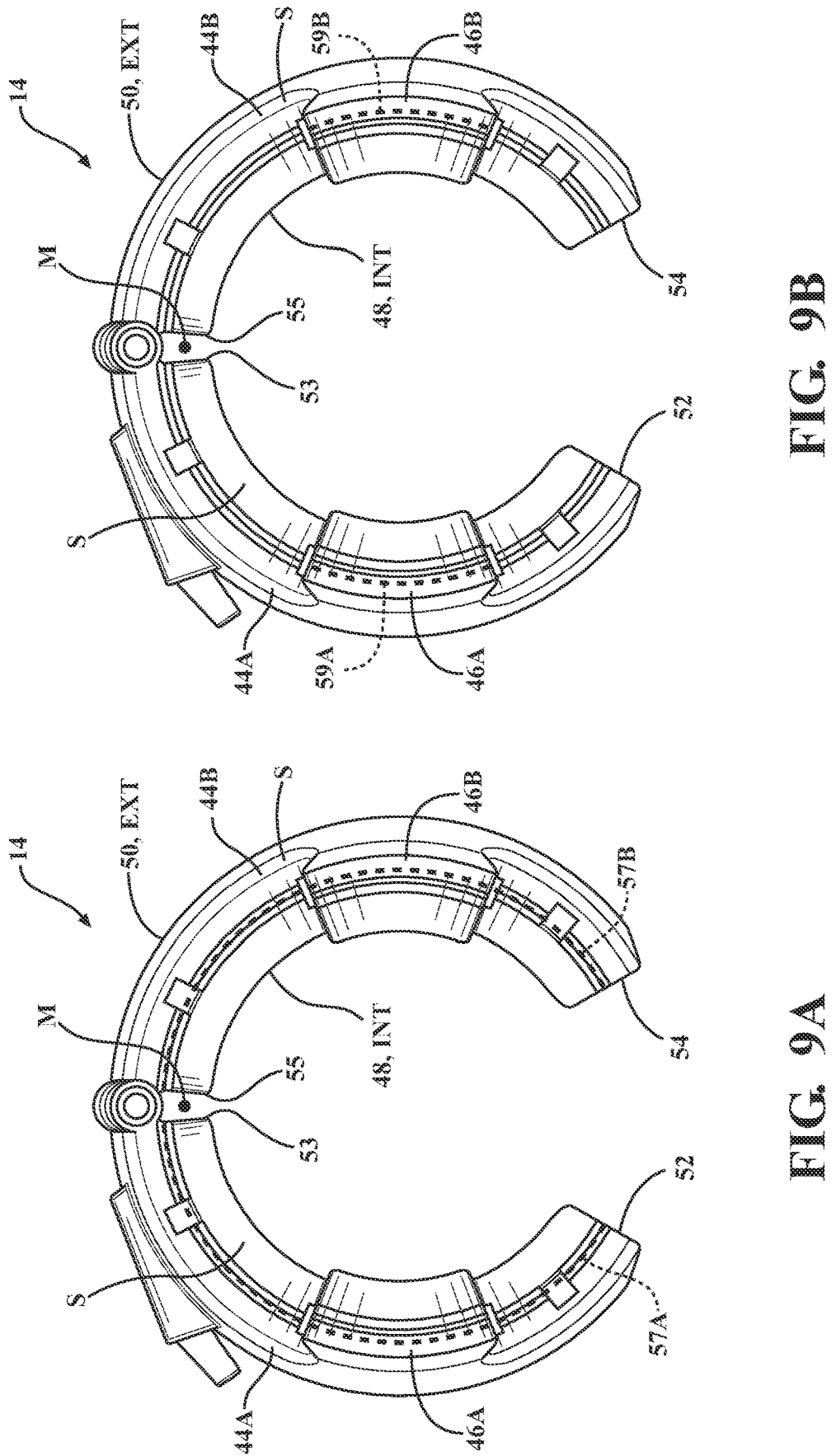
FIGS. 9A and 9B are side view of the tracking apparatus illustrating an arcuate length of the body of the tracking apparatus and an arcuate length of a first wing portion and a second wing portion of the tracking apparatus.

FIGS. 9A and 9B further illustrate a size of the first and second wing portions 46A, 46B with respect to the first and second arms 44A, 44B. As shown, a side S of the first arm 44A includes a side surface length 57A and a side S of the second arm 44B includes a side surface length 57B. The side surface length 57A is defined between the first distal end 52 of the body 44 and a first proximal end 53 of the body 44, the first proximal end 53 being proximal to a midpoint M of the body 44 located between the first distal end 52 and the second distal end 54. The side surface length 57B is defined between the second distal end 54 of the body 44 and a second proximal end 55 of the body 44, the second proximal end 55 being proximal to the midpoint M. Additionally, the first wing portion 46A includes first wing portion length 59A between the midpoint M and first distal end 52 and the second wing portion 44B includes second wing portion length 59B between the midpoint M and second distal end 54. As shown, the first and second wing portion lengths 59A, 59B are less than the first and second side surface lengths 57A, 57B. In the instance of FIGS. 9A and 9B, the first and second side surface lengths 57A, 57B include the first and second wing portion lengths 59A, 59B. In some instances, the first wing portion length 59A may be greater than or less than the second wing portion length 59B. Furthermore, a size of the lengths 57A, 57B, 59A, 59B may vary from the size shown in FIGS. 9A and 9B.

In the instance of FIG. 3, the first and second arms 44A, 44B are of substantially similar sizes. Similarly, the first and second wing portions 46A, 46B are of substantially similar sizes. However, in other instances, the first and second arms 44A, 44B may be of differing sizes and the first and second wing portions 46A, 46B may be of differing sizes. For example, the side surface length 57A of the first arm 44A may differ from the side surface length 57B of the second arm 44B and the axial length 73A of the first arm 44A may differ from the axial length 73B of the second arm 44B. Similarly, the arcuate length 59A of the first wing portion 46A may differ from the arcuate length 59B of the second wing portion 46B and the axial length 75A of the first wing portion 46A may differ from the axial length 75B of the second wing portion 46B.

In the instance of FIG. 3, the first and second wing portions 46A, 46B each include an arcuate configuration. In other instances, the first wing portion 46A, and the second wing portion 46B may include any suitable configuration. Furthermore, the first wing portion 46A, and the second wing portion 46B may include differing configurations.

The first and second wing portions 46A, 46B may extend from the first and/or second arm 44A, 44B at any location along the body 44. Referring to FIG. 3, the first wing portion 46A may extend from the first arm 44A at any location between the midpoint M and the first distal end 52 and the second wing portion 46B may extend from the second arm 44B at any location between the midpoint M and the second distal end 54. In a more specific instance, the first wing portion 46A may extend from the first and/or second arm 44A, 44B at a location separated from the second wing portion 46B. As shown in FIG. 3, the first wing portion 46A may be located halfway between the first distal end 52 and the midpoint M and the second wing portion 46B may be located halfway between the midpoint M and the second distal end 54 such that the interior surfaces INT of the first and second wing portions 46A, 46B face one another, as shown in FIG. 3, for example. In other instances, the first and second wing portions 46A, 46B may be located such that a portion of the interior surfaces INT of the first and second wing portions 46A, 46B face one another or such that the interior surfaces INT of the first and second wing portions 46A, 46B do not face one another. In still other instances, both of the first and second wing portions 46A, 46B may extend from the first and/or second arm 44A, 44B at a location between the first distal end 52 and the midpoint M and/or between the midpoint M and the second distal end 54.

Additionally, the first and second wing portions 46A, 46B may be connected to one another. For example, in one instance, the first and second wing portions 46A, 46B may each include a portion perpendicular to the axis AX that are connected to one another such that the first and second wing portions 46A, 46B are connected to one another. In another instance, the tracking apparatus 14 may include a second body 44 (not shown) and the first and second wing portions 46A, 46B may be connected to one another via the second body 44. Said differently, a side S of the second body 44 may be connected to a side S of the first body 44 by the first and second wing portions 46A, 46B.

The location of the first and second wing portions 46A, 46B relative to one another offers an advantage of the tracking system 10. As previously stated, the first wing portion 46A extends from the first and/or second arm 44A, 44B at a location separated from the second wing portion 46B. In this way, the tracking apparatus 14 includes a window 78 between the first wing portion 46A and the second wing portion 46B, as shown in FIGS. 3 and 4. As such, a surgeon is able to view the surgical site and the patient limb without obstruction during a surgical procedure while the tracking apparatus 14 is coupled to the patient 12. Advantageously, in instances where the tracking system 10 is a part of the robotic surgical system 24, the manipulator 26 may be configured to carry out a surgical procedure on the patient limb without obstruction while the tracking apparatus 14 is coupled to the patient 12.

The tracking apparatus 14 includes one or more ultrasonic sensors 48. As shown in FIG. 3, the ultrasonic sensors 48 may be coupled to both the interior surface INT of the first and second arms 44A, 44B and the interior surface INT of the first and second wing portions 46A, 46B. The ultrasonic sensors 48 are configured to transmit ultrasonic waves to and receive ultrasonic waves from the bone of the patient 12. The ultrasonic sensors 48 are located on the interior surface INT such that ultrasonic waves transmitted by the ultrasonic sensors 48 are directed towards the patient limb L.

The ultrasonic sensors 48 coupled to the first and second wing portions 46A, 46B offer an advantage of the tracking system 10. As previously stated, the first and second wing portions 46A, 46B extend from the first and/or second arm 44A, 44B in a manner substantially parallel (+/−30 degrees) to the bone axis BAX. As such, the first and second wing portions 46A, 46B allow a greater number of ultrasonic sensors 48 to transmit ultrasonic waves 80 to and receive ultrasonic waves 80 from the bone of the patient 12, in comparison to a tracking apparatus 14 without the first and second wing portions 46A, 46B. Additionally, the first and second wing portions 46A, 46B allow ultrasonic waves 80 to be transmitted to and received from a greater amount of the bone of the patient 12, enabling greater ultrasonic sensing coverage along the length of the bone. As such, the one or more controllers 20 coupled to the ultrasonic sensors 48 may determine a shape of a greater amount of the bone and a position of a greater amount of the bone.

The tracking apparatus 14 may include any suitable number of ultrasonic sensors 48. For illustrative purposes, four ultrasonic sensors 48 are shown in the tracking apparatus 14 of FIG. 3. In other instances, the tracking apparatus 14 may include one, two, five, ten, or fifty ultrasonic sensors 48. The tracking apparatus 14 may include a number of ultrasonic sensors 48 suitable for adequate ultrasonic sensing of the bone of the patient 12.

Figures 10A, 10B:
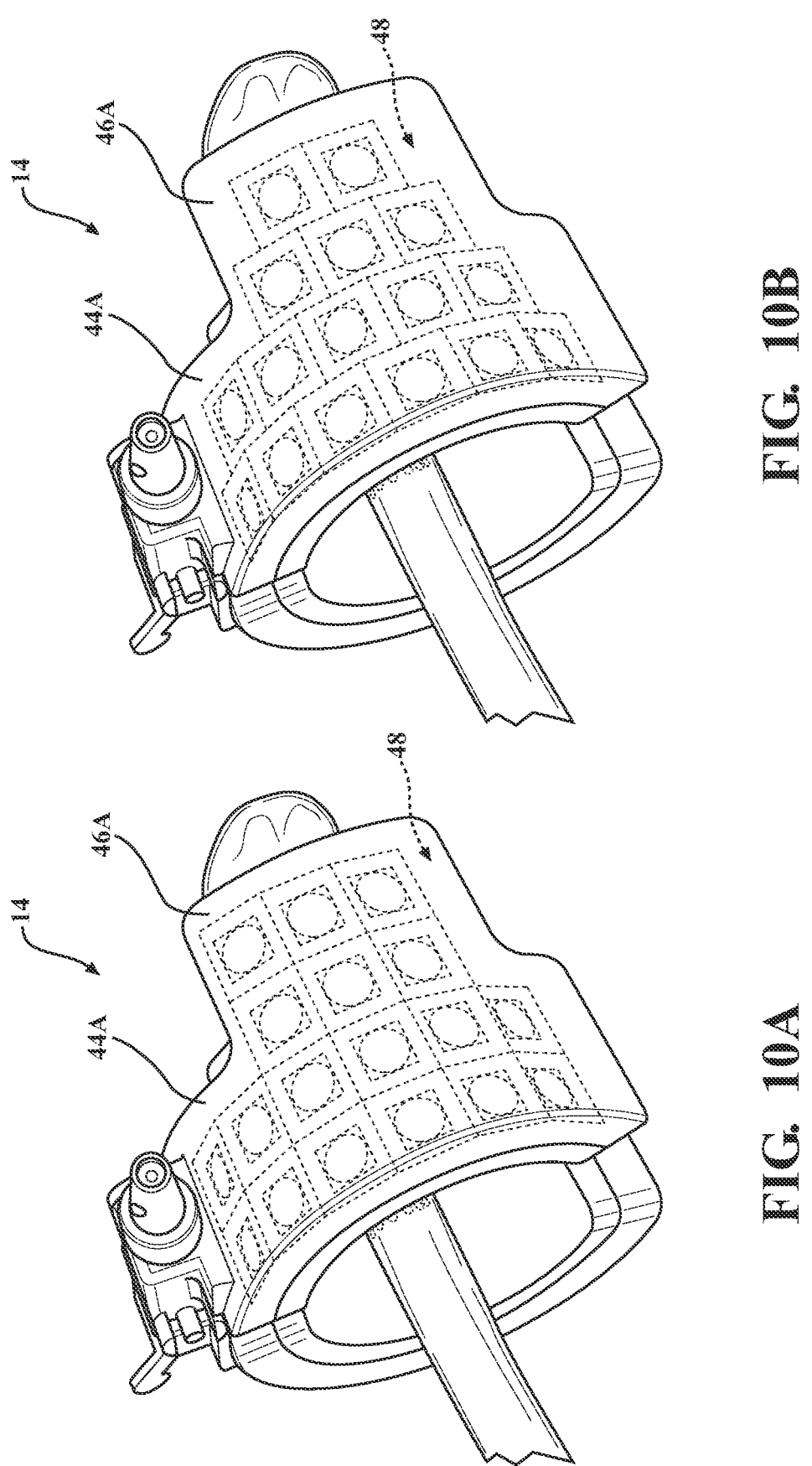
FIGS. 10A-10B are diagrammatic views of the tracking apparatus, wherein various arrangements of ultrasonic sensors are illustrated.

The ultrasonic sensors 48 may be arranged in any suitable fashion. For example, as shown in FIG. 3, the ultrasonic sensors 48 may be arranged in two one-dimensional arrays. As shown in FIG. 10A, the ultrasonic sensors 48 may be arranged in a two-dimensional array. As shown in FIG. 10B, the ultrasonic sensors 48 may be arranged in an offset two-dimensional array. The ultrasonic sensors 48 may also be arranged in a predetermined arrangement, such as a checkerboard arrangement. The ultrasonic sensors 48 may also be arranged in a random arrangement.

Figure 11:
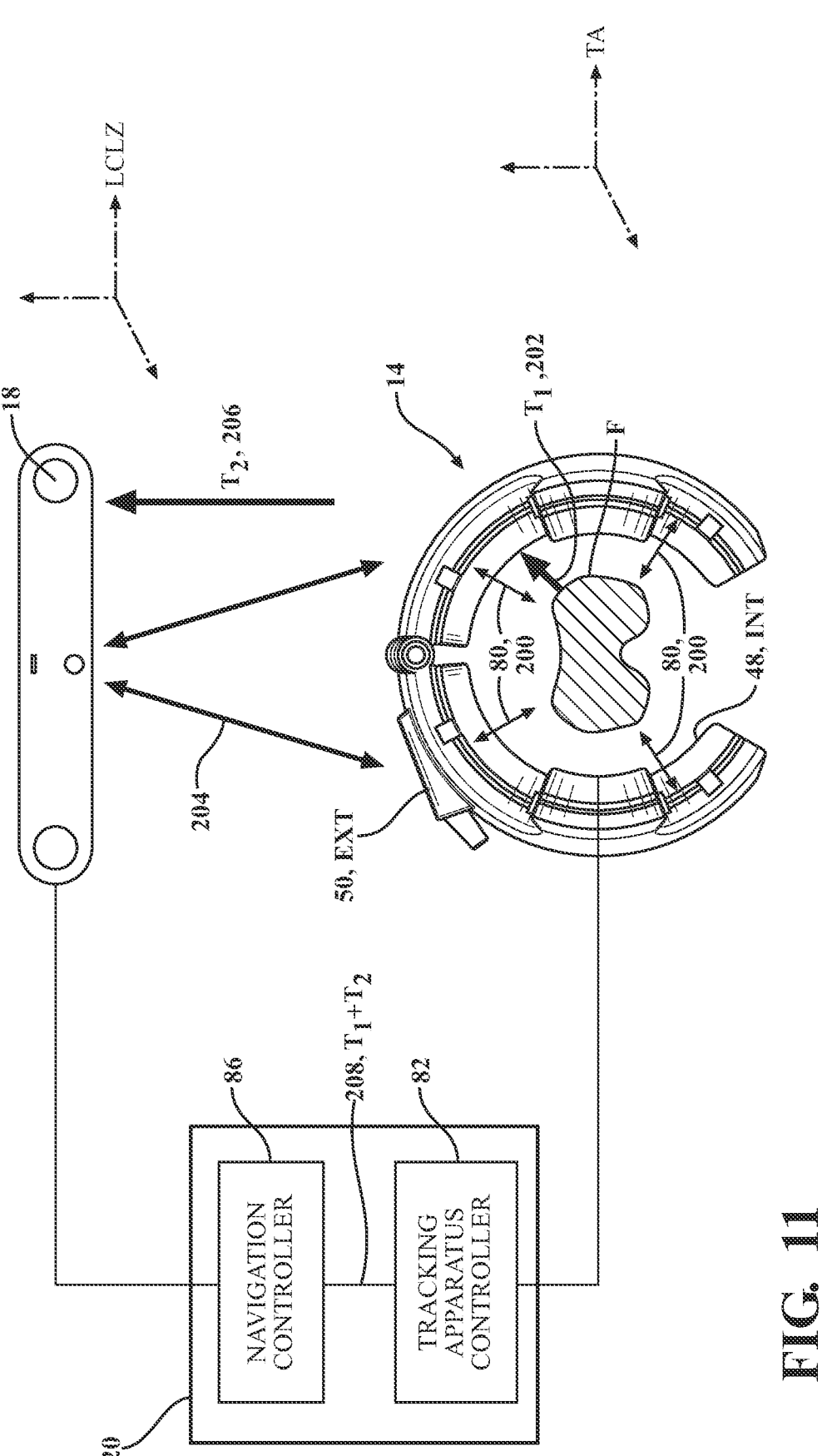
FIG. 11 is a block diagram of the tracking system, wherein a controller of the tracking system is illustrated.

The ultrasonic sensors 48 are configured to transmit ultrasonic waves to and receive ultrasonic waves from the bone and patient soft tissue adjacent to the bone. Referring to FIG. 11, the ultrasonic sensors 48, which are located on the interior surface INT of the first and second arms 44A, 44B are shown transmitting and receiving ultrasonic waves 80 to and from the patient limb, including the bone. As such, the one or more controllers 20 coupled to the ultrasonic sensors 48 may be configured to determine a position of the bone and/or a shape of the bone based on the ultrasonic waves 80 received by the ultrasonic sensors 48 in the tracking apparatus coordinate system TA. Additionally, or alternatively, the one or more controller 20 coupled to the ultrasonic sensors 48 may be configured to identify soft tissue adjacent to the bone to monitor physiological activity of the soft tissue. For instance, the one or more controllers 20 may track motion of the blood vessels of the soft tissue, identify debris entering the blood stream, and/or monitor motion or strain of ligaments.

A model of the bone or a surface of the bone is generated by the one or more controller 20 from the ultrasonic sensor 48 information. The one or more controllers 20 can use any suitable image processing and/or segmentation technique to generate the model. In one instance, the model can be formed using machine learning algorithms. In one example, the surface of the bone can be detected by segmenting the ultrasonic imaging data using a convolutional neural network, as described in US20190069882A1, entitled "Ultrasound Bone Registration with Learning-Based Segmentation and Sound Speed Calibration" the contents of which are hereby incorporated by reference in its entirety.

Figure 12:
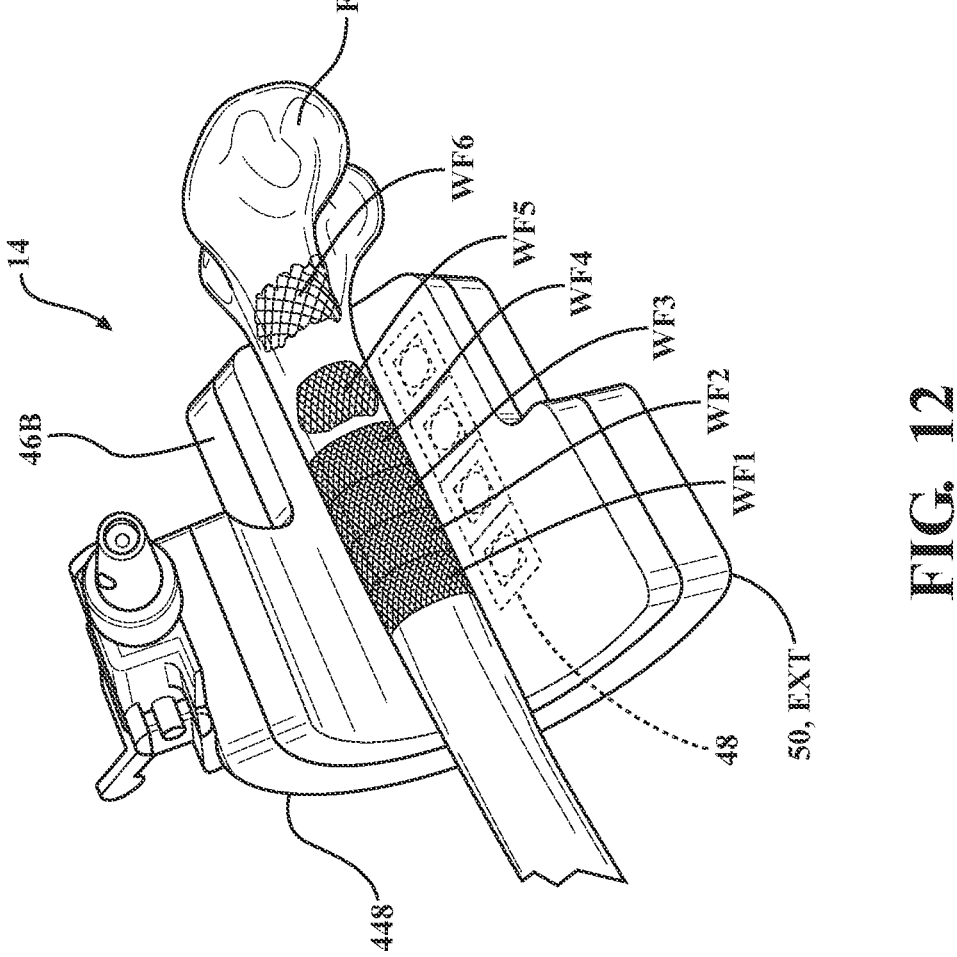
FIG. 12 is a cutaway view of the tracking system, wherein various wave fronts transmitted by the ultrasonic sensors of the tracking apparatus are shown.

The ultrasonic sensors 48 may be configured to transmit the ultrasonic waves 80 using beam forming and beam steering techniques. In this way, the ultrasonic sensor 48 may transmit the ultrasonic waves 80 in a manner that maximizes information response. For example, the ultrasonic sensors 48 may be configured to steer and form a beam to produce an ultrasonic wave front that conforms to the surface of the bone of the patient 12. For example, FIG. 12 illustrates an instance where the ultrasonic sensors 48 transmit ultrasonic waves 80 with wave fronts WF1-WF6. As shown, the wave fronts WF1-WF6 conform to various surfaces along the femur F. In this way, the ultrasonic sensors 48 maximize the intensity of the ultrasonic waves 80 reflected off the femur F, enabling the one or more controllers 20 coupled to the ultrasonic sensors 48 to more accurately determine a shape of the bone and a position of the bone. The ultrasonic sensors 48 can be spatially calibrated to reflect a variation in propagation speed of the ultrasound waves through the bone by comparing steered frames of the ultrasound imaging. The ultrasonic sensors 48 can also be temporally calibrated by creating a point cloud of the surface and calculating a set of projection values of the point cloud to a vector. These calibration techniques are described in US20190069882A1, entitled "Ultrasound Bone Registration with Learning-Based Segmentation and Sound Speed Calibration" the contents of which are hereby incorporated by reference in its entirety.

As shown throughout the Figures, the tracking apparatus 14 includes trackable elements 50. As shown in FIG. 3, for example, the trackable elements 50 are coupled to, fixed, or otherwise or located on, the exterior surface EXT of the body 44 and the exterior surface EXT of the first and second wing portions 46A, 46B. The navigation localizer 18 of the navigation system 16 is configured to track the tracking apparatus 14 by tracking the trackable elements 50. The one or more controller 20 may then determine a position of the tracking apparatus 14 and a position of the bone of the patient 12 in the localizer coordinate system LCLZ based on the navigation localizer 18 tracking the trackable elements 50.

The trackable elements 50 coupled to the first and second wing portions 46A, 46B offer an advantage of the tracking system 10. As previously stated, the first and second wing portions 46A, 46B extend from the first and/or second arm 44A, 44B along the bone axis BAX. As such, the first and second wing portions 46A, 46B allow a greater number of trackable elements 50 to be coupled to the tracking apparatus 14 and tracked by the localizer 18, in comparison to a tracking apparatus 14 without the first and second wing portions 46A, 46B. Since these trackable elements 50 are on/in the first and second wing portions 46A, 46B, greater tracking accuracy is achieved since the trackable elements 50 cover a greater length of the bone along the bone axis BAX. As such, the one or more controllers 20 coupled to the navigation localizer 18 may determine the position of the tracking apparatus 14 in the localizer coordinate system LCLZ with increased accuracy.

The tracking apparatus 14 may include any suitable number of trackable elements 50. In the instance of FIG. 3, six trackable elements 50 are shown on the second arm 44B and one trackable element 50 is shown on the second wing portion 46B. In other instances, the tracking apparatus 14 may include a total of one, two, five, ten, or fifty trackable elements 50 arranged on the body 44 and the first and second wing portions 46A, 46B.

Figures 10C, 10D:
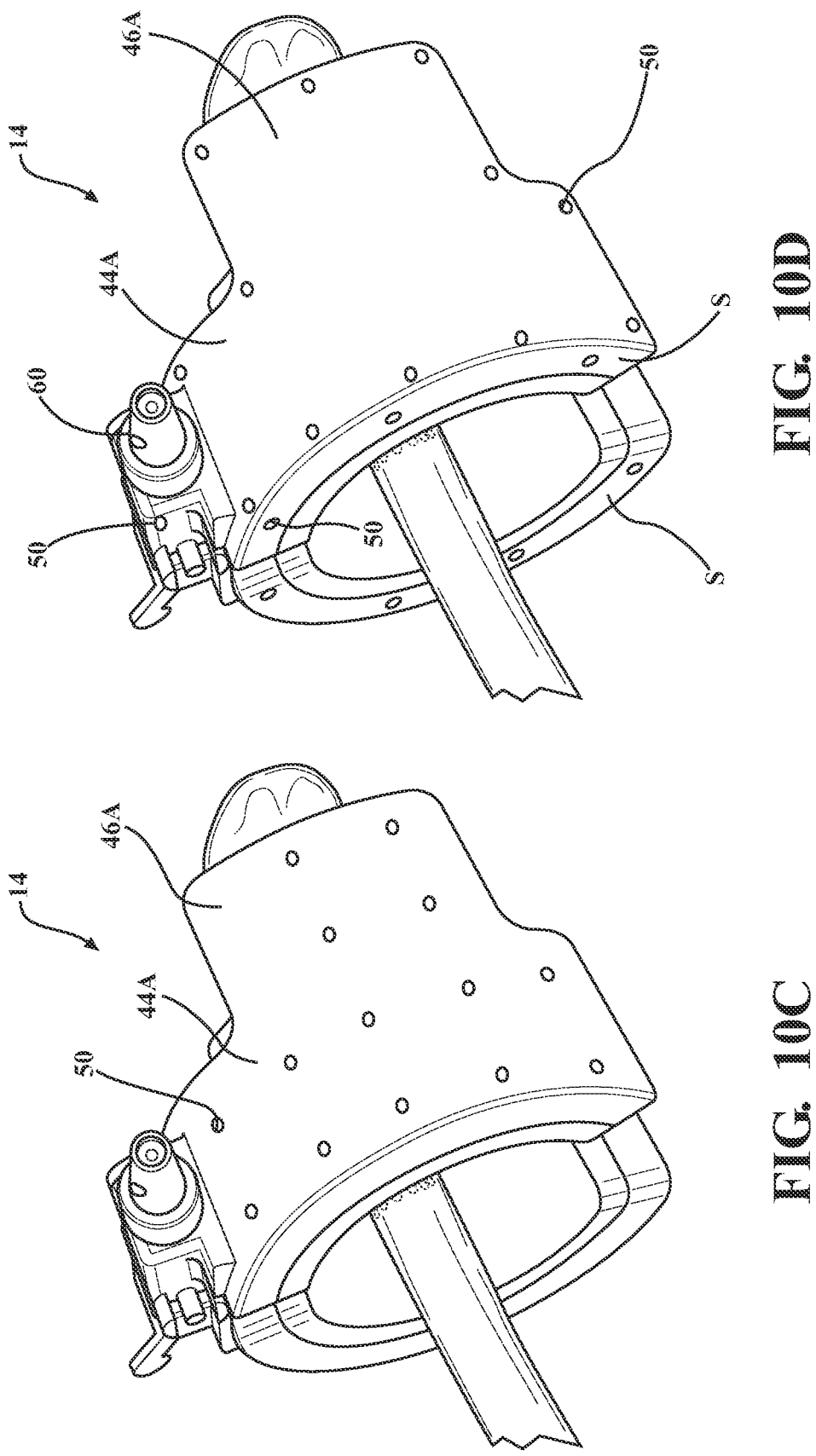
FIGS. 10C-10D are diagrammatic views of the tracking apparatus, wherein various arrangements of trackable elements are illustrated.

The trackable elements 50 may be arranged in any suitable manner. In the instance of FIG. 3, the six trackable elements 50 of the second arm 44B are arrange in a 2-by-3 array. In other instances, the trackable elements 50 may be arranged in any suitable m-by-n array, with "m" and "n" being greater than or equal to one. For example, in FIG. 10C, the trackable elements 50 are arranged in a 2-by-2 array, a 2-by-4 array, and a 1-2 array along the first arm 44A and the first wing portion 46A. The trackable elements 50 may also be arranged in any predetermined fashion to provide adequate tracking of the tracking apparatus 14 by the localizer 18. For example, in FIG. 10D, the trackable elements 50 are arranged along a perimeter of the first arm 44A and the first wing portion 46A.

The trackable elements 50 may be located on exterior surface EXT of the body 44 and the exterior surface EXT of the first and second wing portions 46A, 46B in any suitable manner. For example, the trackable elements 50 may be rigidly fixed to the exterior surface EXT, located atop the exterior surface EXT, embedded below the exterior surface EXT, or the like. Alternatively, the trackable elements 50 can be located underneath the exterior surface EXT such that the trackable elements 50 are enclosed by the housing of the body 44. Additionally, the trackable elements 50 may be located on any other suitable component of the tracking apparatus 14. For example, in FIG. 10D, the trackable elements are located on a side S of the first arm 44A and on the hinge 60 of the tracking apparatus 14.

The trackable elements 50 may be any suitable type of trackable element. For example, the trackable elements 50 may be any optical trackable element configured to be sensed by an optical localizer, such as the navigation localizer 18. As one example, any one or more of the trackable elements 50 may include active markers. The active markers may include light emitting diodes (LEDs). Alternatively, or additionally, the trackable elements 50 may have passive markers, such as reflectors, which reflect light emitted from the navigation localizer 18. Furthermore, other suitable markers not specifically described herein may be utilized.

In one example, the trackable elements 50 may be radio frequency (RF) sensors or emitters which can be detected by an RF localizer 18. In such an example, the navigation system 16 and/or localizer 18 may be RF-based. For example, the navigation system 16 may comprise an RF transceiver coupled to the navigation controller 86. The tracking apparatus 14, the manipulator 26, the tool 40, and/or the patient 12 may comprise RF emitters or transponders attached thereto. The RF emitters or transponders may be passive or actively energized. The RF transceiver may transmit an RF tracking signal and generate state signals to the navigation controller 72 based on RF signals received from the RF emitters. The navigation controller 72 may analyze the received RF signals to associate relative states thereto. The RF signals may be of any suitable frequency. The RF transceiver may be positioned at any suitable location to sense the objects using RF signals effectively. Furthermore, the RF emitters or transponders may have any suitable structural configuration that may be much different than the trackable elements 50 of the tracking apparatus 14.

In another example, the trackable elements 50 may be electromagnetic (EM) sensors or emitters which can be detected by an EM localizer 18. In such an example, the navigation system 16 and/or localizer 18 may be electromagnetically based. For example, the navigation system 16 may comprise an EM transceiver coupled to the navigation controller 86. The tracking apparatus 14, the manipulator 26, the tool 40, and/or the patient 12 may comprise EM components attached thereto, such as any suitable magnetic tracker, electro-magnetic tracker, inductive tracker, or the like. The trackers may be passive or actively energized. The EM transceiver may generate an EM field and generate state signals to the navigation controller 86 based upon EM signals received from the trackers. The navigation controller 86 may analyze the received EM signals to associate relative states thereto. Again, such examples of the navigation system may have structural configurations that are different than the navigation system 16 configuration shown in FIG. 1.

In yet another example, the trackable elements 50 may include patterns or features (e.g., barcodes, QR codes, perturbations, surface markings, etc.) on the exterior surface EXT which can be detected by a machine-vision camera localizer 18. In such an example, the navigation system 16 may be a machine-vision based. For example, the machine-vision camera localizer 18 may include a machine-vision camera configured to detect the patterns or features of the trackable elements 50. The patterns or features may be passive or actively energized. The machine-vision camera may generate state signals to the navigation controller 86 based upon detecting the patterns or features of the trackable elements 50. The navigation controller 86 may analyze the patterns or features to associate relative states thereto. Again, such examples of the navigation system 16 may have structural configurations that are different than the navigation system 16 configuration shown in FIG. 1.

The tracking apparatus 14 may include a tracking apparatus controller 82, or other type of control unit. Referring to FIG. 1, the tracking apparatus controller 82 may be a controller of the one or more controllers 20. The tracking apparatus controller 82 may comprise one or more computers, or any other suitable form of controller configured to determine a shape of a bone of the patient 12 and/or a position of a bone of the patient 12. The tracking apparatus controller 82 may have a central processing unit CPU and/or other processors, memory MEM, and storage (not shown). The tracking apparatus controller 82 is loaded with software as described below. The processors could include one or more processors to control operation of the tracking apparatus 14, such as an operation of the ultrasonic sensors 48 and/or the trackable elements 50. The processors can be any type of microprocessor, multi-processor, and/or multi-core processing system. The tracking apparatus controller 82 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any implementation to a single processor. The tracking apparatus 14 may also comprise a user interface UI with one or more displays 22 (shown in FIG. 2) and/or input devices (e.g., push buttons, keyboard, mouse, microphone (voice-activation), gesture control devices, touchscreens, etc.).

The tracking system 10 may include more than one tracking apparatus 14. For example, referring to FIG. 12, the tracking system 10 includes a first tracking apparatus 14', and a second tracking apparatus 14". The first tracking apparatus 14' is configured to track the femur F of the patient 12 such that the body 44 of the first tracking apparatus 14' is configured to couple to the femur F of the patient 12. The second tracking apparatus 14" is configured to track the tibia T of the patient 12 such that the body 44 of the second tracking apparatus 14" is configured to couple to the tibia T of the patient 12. In this way, the tracking system 10 may track both the femur F and the tibia T of the patient 12.

D. Example Control System

Referring to FIG. 2, the tracking system 10 includes one or more controllers 20. In the instance of FIGS. 1 and 2, the one or more controllers 20 includes the tracking apparatus controller 82 of the tracking apparatus 14 and the navigation controller 86 of the navigation system 16. Additionally, the one or more controllers 20 of the tracking system 10 may include the manipulator controller 38 and/or the tool controller 42. The one or more controllers 20 may be configured to communicate via a wired bus or communication network, as shown in FIG. 2, via wireless communication, or otherwise.

The one or more controllers 20 further includes one or more software programs and software modules shown in FIG. 2. The software modules may be part of the program or programs that operate on the tracking apparatus controller 82, the navigation controller 86, the manipulator controller 38, the tool controller 42, or any combination thereof, to process data to assist with tracking a bone of a patient limb with the tracking system 10. The software programs and/or modules include computer readable instructions stored in non-transitory memory MEM on the tracking apparatus controller 82, the navigation controller 86, the manipulator controller 38, the tool controller 42, or any combination thereof, to be executed by one or more processors MEM of the controllers 38, 42, 82, 86. The memory MEM may be any suitable configuration of memory, such as RAM, non-volatile memory, etc., and may be implemented locally or from a remote database. Additionally, software modules for prompting and/or communicating with the user may form part of the program or programs and may include instructions stored in memory MEM on the tracking apparatus controller 82, the navigation controller 86, the manipulator controller 38, the tool controller 42, or any combination thereof. The user may interact with any of the input devices of the navigation user interface UI or other user interface UI to communicate with the software modules. The user interface software may run on a separate device from the tracking apparatus controller 82, the navigation controller 86, the manipulator controller 38, the tool controller 42, or any combination thereof.

The one or more controllers 20 may comprise any suitable configuration of input, output, and processing devices suitable for carrying out the functions and methods described herein. The one or more controllers 20 may comprise one or more of the tracking apparatus controller 82, the navigation controller 86, the manipulator controller 38, and the tool controller 42. Additionally, these controllers 38, 42, 82, 86 may communicate via a wired bus or communication network, as shown in FIG. 2, via wireless communication, or otherwise. For example, the tracking apparatus controller 82 may receive ultrasound data from the ultrasonic sensors 48 and transmit the ultrasound data to the navigation controller 86 via wireless communication such that the navigation controller 86 may process the ultrasound data and determine the position of the bone of the patient 12. In another example, the navigation controller 86 may track the trackable elements 50 and transmit tracking data to the tracking apparatus controller 82 via wireless communication such that the tracking apparatus controller 82 may process the tracking data and determine the position of the bone of the patient 12. As used herein, the term "one or more controllers 20" may refer to any one or all of the tracking apparatus controller 82, the navigation controller 86, the manipulator controller 38, the tool controller 42, or any combination thereof. The one or more controllers 20 may comprise one or more microcontrollers, field programmable gate arrays, systems on a chip, discrete circuitry, sensors, displays, user interfaces, indicators, and/or other suitable hardware, software, or firmware that is capable of carrying out the functions described herein.

Figure 13:
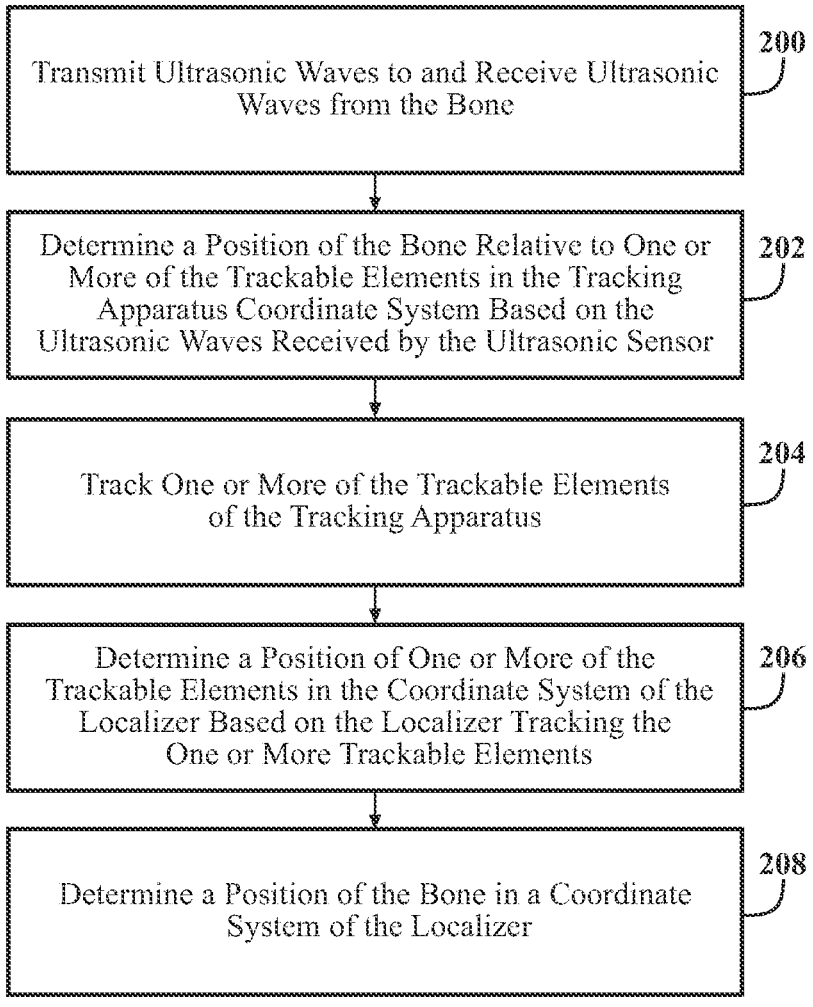
FIG. 13 is a flow chart illustrating a method of operating the tracking system, according to one implementation.

The one or more controllers 20 of the tracking system 10 are configured to perform steps 200-208 shown in FIGS. 11 and 13. Generally, steps 200-208 describe a configuration of the tracking system 10 to transform a state of a bone of a patient 12 from the tracking apparatus coordinate system TA to the localizer coordinate system LCLZ.

As shown in FIG. 11, the one or more controllers 20 are coupled to the ultrasonic sensors 48 of the tracking apparatus 14 and to the localizer 18. Specifically, in the instance of FIG. 11, the one or more controllers 20 include the tracking apparatus controller 82, which is coupled to the ultrasonic sensors 48, and the navigation controller 86, which is coupled to the localizer 18.

Referring to FIG. 13, during step 200, the ultrasonic sensors 48 are configured to transmit ultrasonic waves 80 to and receive ultrasonic waves 80 from the bone. As shown in FIG. 11, the ultrasonic sensors 48 are configured to transmit ultrasonic waves 80 to the femur F and receive ultrasonic waves 80 reflected off the femur F during step 200.

Referring to FIG. 13, during step 202, the one or more controllers 20 are configured to determine a state of the bone relative to one or more of the trackable elements 50 in the tracking apparatus coordinate system TA based on the ultrasonic waves 80 received by the ultrasonic sensor 48. This is performed using a first transform T1 from the bone to coordinate system of the tracking apparatus 14. Specifically, the location of the ultrasonic sensors 48 on the tracking apparatus 14 are defined according to a predetermined configuration, which can be stored in memory of the controller(s) 20. Moreover, the location of the trackable elements 50 on the tracking apparatus 14 are defined according to a predetermined configuration, which can be stored in memory of the controller(s) 20. Accordingly, the location of each ultrasonic sensor 48 can be known relative to each trackable element 50 according to this fixed data. In the instance of FIG. 11, the tracking apparatus controller 82 determines, during step 202, the position of the bone (e.g., femur F) relative to the trackable elements 50 in the tracking apparatus coordinate system TA based on the ultrasonic waves 80 received by the ultrasonic sensors 48. In instances where the one or more controllers 20 do not include the tracking apparatus controller 82, any other controller 20 may perform step 202.

Referring to FIG. 13, during step 204, the localizer 18 is configured to sense one or more of the trackable elements 50. During step 206, the one or more controllers 20 are configured to determine a state of one or more of the trackable elements 50 in the localizer coordinate system LCLZ based on the localizer 18 tracking the one or more trackable elements 50 during step 204. This is performed using a second transform T2, shown in FIG. 11, from the tracking elements 50 of the tracking apparatus 14 to the localizer 18. In the instance of FIG. 11, the navigation controller 86 determines, during step 206, the position of the trackable elements 50 in the localizer coordinate system LCLZ based on the localizer 18 tracking the trackable elements 50. In instances where the one or more controllers 20 do not include the navigation controller 86, any other controller 20 may perform step 206.

Referring to FIG. 13, during step 208, the one or more controllers 20 are configured to determine a state of the bone in the localizer coordinate system LCLZ. This is performed by combining the first transform T1 with the second transform T2 to transform the position of the femur F from the tracking apparatus coordinate system TA to the localizer coordinate system LCLZ. This combination of transforms T1, T2 is illustrated as "T1+T2" in FIG. 11. During step 208, the one or more controllers 20 combines the position of the femur F in the tracking apparatus coordinate system TA (an output of the first transform T1), as determined by the tracking apparatus controller 82 in step 202, and the position of the trackable elements 50 in the localizer coordinate system LCLZ (an output of the second transform T2), as determined by the navigation controller 86 in step 206, to determine the position of the femur F in the localizer coordinate system LCLZ. In some instances, the tracking apparatus controller 82 may communicate with the navigation controller 86 and one of the tracking apparatus controller 82 and the navigation controller CPU performs step 208. In instances where the one or more controllers 20 do not include the navigation controller 86 and/or the tracking apparatus controller 82, any other controller 20 may perform step 208.

In instances where the tracking system 10 is a part of the robotic surgical system 24, the controller(s) 20 may be configured to further transform the position of the bone of the patient 12 from the localizer coordinate system LCLZ to the manipulator coordinate system MNPL, shown in FIG. 1. The robotic surgical system 24 may then control the manipulator 26 based on the position of the bone in the manipulator coordinate system MNPL. For example, the manipulator controller 38 and/or the tool controller 42 may control the robotic surgical system 24 during the manual mode or the semi-autonomous mode based on the position of the bone in the manipulator coordinate system MNPL. In some instances, the tracking apparatus controller 82 and/or the navigation controller 86 may perform the transformation of the position of the bone from the localizer coordinate system LCLZ to the manipulator coordinate system MNPL. The tracking apparatus controller 82 and/or the navigation controller 86 may then communicate the position of the bone in the manipulator coordinate system MNPL to the manipulator controller 38. In some instances, the tracking apparatus controller 82 and/or the navigation controller 86 may be configured to communicate the position of the bone in the localizer coordinate system LCLZ to the manipulator controller 38, which transforms to determine the position of the bone from the localizer coordinate system LCLZ to the manipulator coordinate system MNPL.

In some instances, the one or more controllers 20 may receive and store a shape of the bone of the patient 12 prior to determining a position of the bone. For instance, the one or more controllers 20 may store a shape of a femur F in a non-transitory memory, such as memory MEM. The shape of the femur F may be specific to the patient 12 to undergo the surgical procedure. The shape of the femur F may be derived by utilizing an algorithm to compare the ultrasonic imaging data to a statistical model or atlas of bone data from one or more populations. The ultrasonic sensors 48 may then transmit ultrasonic waves 80 using beam forming and beam steering techniques based on the stored shape of the femur F to maximize information response. For example, the ultrasonic sensors 48 may be configured to steer and form a beam to produce an ultrasonic wave front that conforms to the surface of the femur F the patient 12 based on the stored shape of the femur F. In this way, the ultrasonic sensors 48 maximize the intensity of the ultrasonic waves 80 reflected off the bone, allowing for a controller 20 coupled to the ultrasonic sensors 48 to more accurately determine a shape of the bone and a position of the bone.

Figure 14:
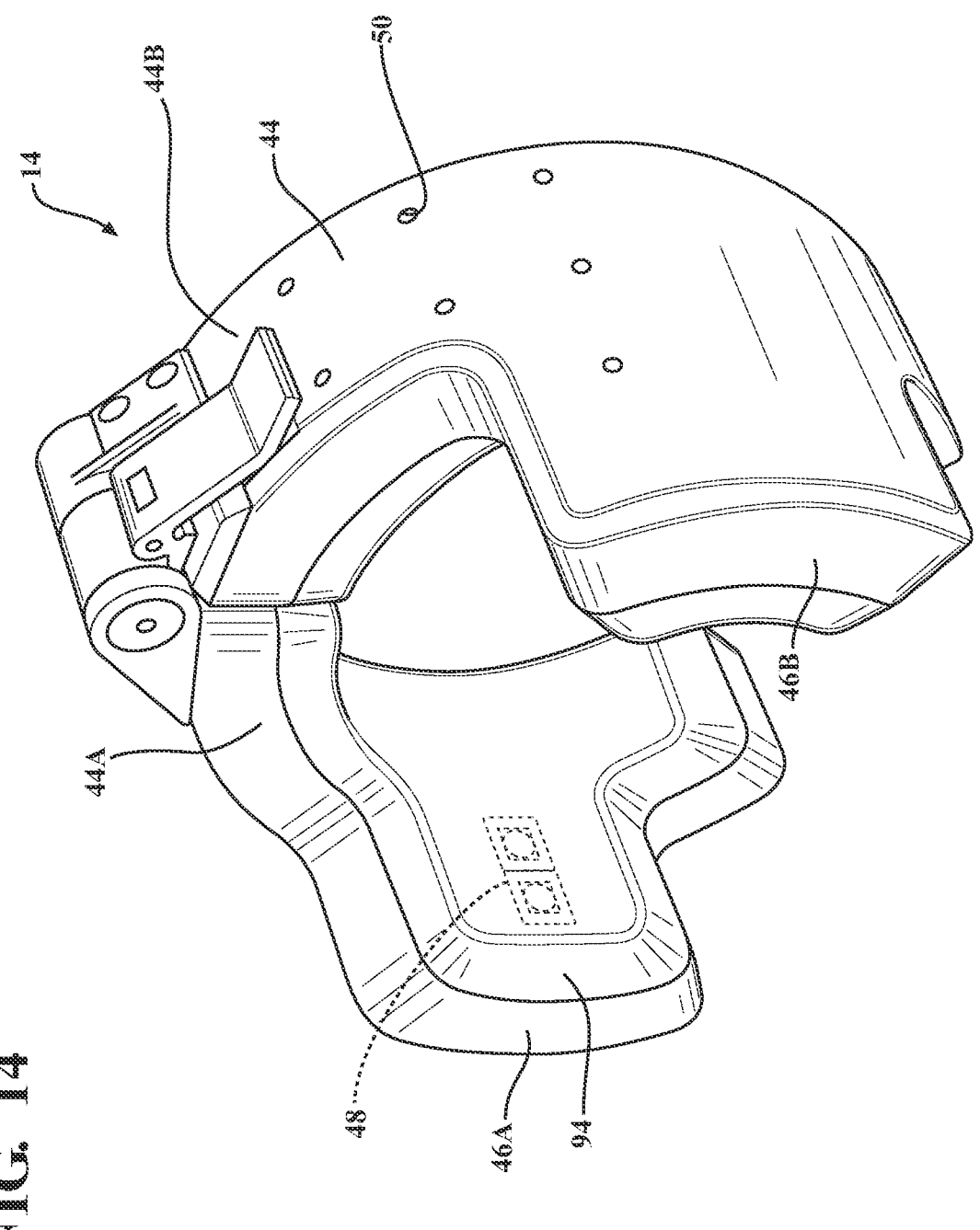
FIG. 14 is a perspective view of an implementation of the tracking apparatus, wherein the tracking apparatus includes a cushion.

In some instances, the tracking apparatus 14 may include a cushion 94. As shown in FIG. 14, the cushion may be coupled to the interior surface INT of the body 44, and optionally, the interior surface INT of the first and second wing portions 46A, 46B. When the body 44 is coupled to the patient 12, the cushion 94 contacts the skin of the patient limb. The cushion 94 is configured to maintain contact integrity between the patient limb and the interior surface INT, which allows for improved transmission and reception of the ultrasonic waves 80 and reduced interference. Advantageously, the cushion 94 is configured to maintain contact integrity between the interior surface INT and patient limbs of a variety of shapes and sizes.

The cushion 94 may include any suitable shape for maintaining contact integrity between the patient limb and the interior surface INT. For example, the cushion may include an arcuate planar surface as shown in FIG. 14. As another example, the cushion may include any other contoured surface. The cushion 94 may include any suitable material for maintaining contact integrity between the patient limb and the interior surface INT. For example, the cushion 94 may include a gel material, a fibrous material, a fluid material, and/or a polyurethane material, or the like.

Figure 15:
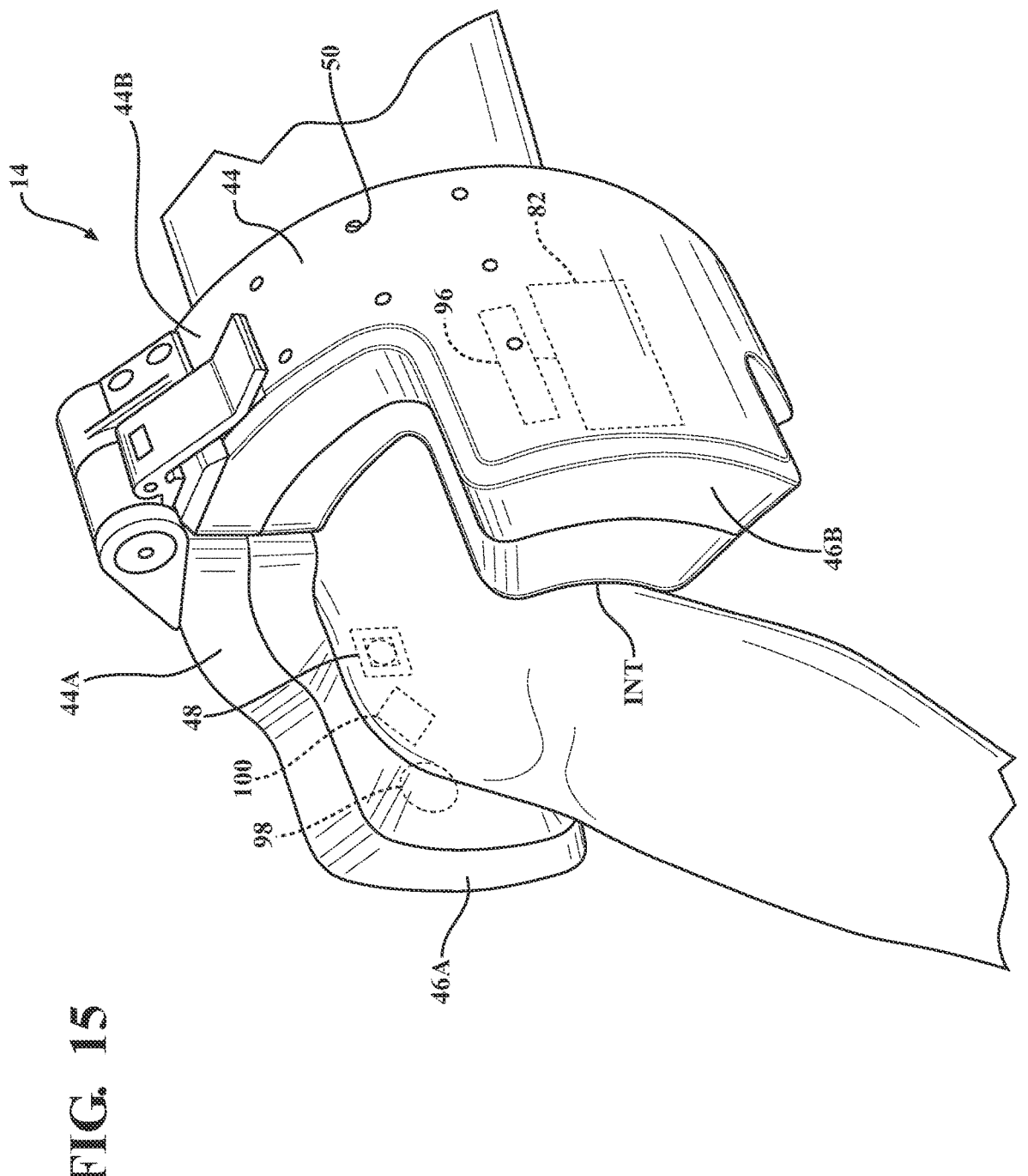
FIG. 15 is a perspective view of an implementation of the tracking apparatus, wherein the tracking apparatus includes a cushion and a fluid control unit.

As shown in FIG. 15, the tracking apparatus 14 may include a fluid control unit 96 coupled to the cushion 94. The fluid control unit 96 may be configured to provide fluid, such as air, water, and/or ultrasonic gel, to the cushion 94. The fluid control unit 96 may provide or remove fluid to the cushion 94 such that the cushion 94 expands or contracts, to enable the cushion 94 to maintain contact integrity between the interior surface INT and a patient limb and to provide additional comfort for the patient. Additionally, during some surgical procedures, it may be advantageous for the cushion 94 to act as a tourniquet. During such surgical procedures, the fluid control unit 96 may provide fluid to the cushion 94 such that the cushion 94 expands to apply sufficient pressure to the patient limb for restricting blood flow.

The fluid control unit 96 may be coupled to, or a part of the one or more controllers 20 either locally coupled to or remotely located from the tracking apparatus 14. In this way, the one or more controllers 20 may control the amount of fluid provided to the cushion 94 by the fluid control unit 96, the speed by which fluid is provided to the cushion 94 by the fluid control unit 96, an amount of fluid drained from the cushion 94 by the fluid control unit 96, and/or a type of fluid provided to the cushion by the fluid control unit 96. In the instance of FIG. 15, the tracking apparatus controller 82 of the one or more controllers 20 is coupled to the fluid control unit 96 and controls an amount of ultrasonic gel provided to the cushion 94 by the fluid control unit 96. Additionally, the fluid control unit 96 may include a user interface UI (not shown) with one or more displays 22 (not shown) and/or input devices (e.g., push buttons, keyboard, mouse, microphone (voice-activation), gesture control devices, touchscreens, etc.).

In some instances, the one or more controllers 20 of the tracking apparatus 14 may be configured to determine an integrity of contact between the patient limb and the interior surface INT of the body 44 and the interior surface INT of the first and second wing portions 46A, 46B. In the instance of FIG. 15, the tracking apparatus controller 82 determines the integrity of contact.

The one or more controllers 20 may determine the integrity of contact between the patient limb and the interior surface INT of the body 44 and the interior surface INT of the first and second wing portions 46A, 46B using a variety of techniques. In one instance, the tracking apparatus controller 82 may determine the integrity of contact based on the ultrasonic waves 80 received by the ultrasonic sensors 48. In another instance, the tracking apparatus 14 may include a light emitter 98 configured to emit light to the patient limb. In such an instance, the tracking apparatus 14 may also include an optical sensor 100 configured to sense light reflected from the patient limb. The tracking apparatus controller 82 may be coupled to the optical sensor 100 and configured to determine the integrity of contact based on the reflected light sensed by the optical sensor 100. For example, the tracking apparatus controller 82 may determine the integrity of contact based on an intensity, a propagation-direction, a frequency, or a wavelength spectrum and polarization of the reflected light. Integrity of contact alternatively can be determined using pressure or distance sensors, or the like, the readings from which can be compared by the one or more controllers 20 to a threshold pressure or distance.

The tracking apparatus 14 may be configured to respond in a variety of ways to the integrity of contact determined by the one or more controllers 20. For example, the tracking apparatus 14 may be configured to adjust the ultrasonic sensors 48 in response to determining the integrity of contact. In one such instance, the tracking apparatus controller 82 may be configured to prevent an ultrasonic sensor 48 from transmitting and receiving ultrasonic waves 80 based on poor integrity of contact. In another instance, the tracking apparatus controller 82 may be configured to control the ultrasonic sensors 48 to steer and form a beam to produce an ultrasonic wave front based on the integrity of contact. As another example, the tracking apparatus controller 82 may be configured to control the fluid control unit 96 based on the integrity of contact. In one such instance, the tracking apparatus 14 may be configured to control an amount of fluid provided to the cushion 94 to achieve a suitable integrity of contact. As yet another example, the tracking apparatus 14 may be configured to notify a surgeon of the integrity of contact. In one such instance, the tracking apparatus 14 may be configured to notify a surgeon that the integrity of contact is acceptable or unacceptable using a user interface UI of the tracking system 10.

The tracking apparatus 14 may also be motorized to move the first and/or second arms 44A, 44B between the open and closed positions 62, 64 and any position therebetween. This may be done to simplify installation of the tracking apparatus 14 to the patient limb L without user assistance. The tracking apparatus 14 may comprise a motor at any one or more of the hinges 60. The one or more controllers 20 may be configured to control the motor based on the integrity of contact as determined by any of the aforementioned sensors. The one or more controllers 20 may initialize motor movement in response to any automated, semi-automated, or manually initiated control signal. The one or more controllers 20 may control the motor to move the first and/or second arms 44A, 44B based on the acceptability or unacceptability of the integrity of contact as determined by any of the aforementioned sensors.

The one or more controller 20 may also be configured to control the tracking apparatus 14 and/or any components of the robotic surgical system 24 based on monitoring physiological activity of soft tissue. As previously stated, the one or more controllers 20 may be configured to identify soft tissue adjacent to the bone to monitor physiological activity of the soft tissue. As an example, the one or more controllers 20 may be configured to control the fluid control unit 96 such that the cushion 94 applies sufficient pressure and restricts blood flow based on the one or more controllers 20 identifying that debris has entered the blood stream. As another example, the one or more controllers 20 may control the tool 40 (e.g., stopping or slowing the tool 40) based on the one or more controllers 20 identifying that debris has entered the blood stream. The one or more controllers 20 may also control the display 22 of a user interface UI to display a warning based on the one or more controllers 20 identifying that debris has entered the blood stream.

The tracking apparatus 14 may also be used for assessing a joint of the patient. This may include joint balancing, joint laxity, joint range of motion, or any other assessment involving kinematics of a joint. The tracking apparatus 14 may do so by tracking the bone, soft tissue, and/or physiological activity of the patient limb L. For instance, ligaments could be identified, and motion or strain of the ligaments could be monitored as part of the joint balancing. In one example, the femur F could be rigidly secured, e.g., to the table or to a joint positioner, while the tracking apparatus 14 is attached to the tibia T. A user could then manipulate the tibia T to assess the joint. Data from the tracking apparatus 14 could be provided to a software program, e.g., a software program implemented by the navigation system 16. The software program could display real-time data involving joint balancing, joint laxity, joint range of motion, or any other assessment involving kinematics of a joint to the user. Alternatively, a tracking apparatus 14 may be placed on the femur F and the tibia T to determine relative motion therebetween for any of the above-described purposes.

The above-described tracking apparatus 14 provides several advantages over conventional means of tracking. The tracking apparatus 14 avoids the need for invasively implanting trackers in the bone of the patient or potential trauma to the patient because the tracking apparatus 14 externally wraps about the skin of the patient limb. The tracking apparatus 14 can be an intelligent component with controllers, calibration, and registration, which avoids the need for additional surgical steps, such as planning the location of the tracker, performing implantation, and performing manual bone registration using a pointer. The tracking apparatus 14 avoids bulky tracking arrays extending out of the surgical site from the bone. The tracking apparatus 14 provides increased visibility of the surgical site and avoids interfere with the surgeon or surgical components of tools in the workspace. For example, the wing portion being to the side of the patient limb provides a "window" of visibility at the top of the joint where surgery is performed. By having a large surface area contact with the patient limb, as well as means for locking or keeping the tracking apparatus 14 in place, the tracking apparatus 14 is less suscep- tible to becoming dislodged or inadvertently moved, which in turn can compromise tracking accuracy. The ultrasound and tracking elements in/on the wing portion of the tracking apparatus 14 provides a greater tracking length along the bone thereby increasing accuracy. In view of the above description, those having skill in the art can appreciate other advantages not specifically described herein.

Several embodiments have been described in the forego- ing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A tracking apparatus for tracking a bone of a patient limb, the tracking apparatus comprising:

a body configured to couple to the patient limb and comprising first and second arms each including an exterior surface, an opposing interior surface, and opposing sides connecting the exterior and interior surfaces, wherein a hinge connects the first arm and the second arm such that the first arm and the second arm are rotatably moveable relative to one another relative to the hinge, and wherein a sensor is configured to sense a relationship between the first and second arms;

a wing portion extending from at least one of the opposing sides of at least one of the first and second arms and the wing portion sharing the interior surface of the at least one first and second arm;

one or more ultrasonic sensors coupled to the interior surface of the first arm, one or more ultrasonic sensors coupled to the interior surface of the second arm, and one or more ultrasonic sensors coupled to the interior surface of the wing portion, each being configured to transmit ultrasonic waves to and receive ultrasonic waves from the bone;

one or more controllers configured to determine a rela- tionship between the one or more of the ultrasonic sensors of the first arm and the one or more of the ultrasonic sensors of the second arm; and one or more trackable elements coupled to the body and the wing portion.

2. The tracking apparatus of claim 1, wherein:

a space is defined between the interior surfaces of the first and second arms for receiving the patient limb;

an axis is defined through the space in a direction extend- ing between the opposing sides;

the wing portion extends along a direction parallel to the axis;

the first and second arms and the wing portion each include an axial length defined along a direction of the axis; and the axial length of the wing portion is greater than or substantially equal to the axial length of the first and second arms.

3. The tracking apparatus of claim 1, wherein the one or more trackable elements includes one or more of:

an optical trackable element configured to be sensed by an optical localizer;

a radio frequency (RF) trackable element configured to be sensed by an RF localizer;

an electromagnetic (EM) trackable element configured to be sensed by an EM localizer; and a pattern or feature configured to be sensed by a machine- vision camera localizer.

4. The tracking apparatus of claim 1, wherein each of the first and second arms and the wing portion has an arcuate configuration.

5. The tracking apparatus of claim 1, wherein the sensor is disposed within the hinge.

6. The tracking apparatus of claim 1, wherein the one or more controllers are configured to calibrate the one or more ultrasonic sensors coupled to the interior surface of the first arm and the one or more ultrasonic sensors coupled to the interior surface of the second arm based on the determined relationship between the first and second arms.

7. The tracking apparatus of claim 1, wherein the first and second arms are integrally connected and are flexible such that the body is configured to move between a closed position and an open position in response to flexing of one or more of the first and second arms.

8. The tracking apparatus of claim 1, wherein the one or more trackable elements are embedded within the exterior surface of one or more of the first and second arms and embedded within the exterior surface of the wing portion.

9. The tracking apparatus of claim 1, wherein the wing portion is further defined as a first wing portion extending from one of the opposing sides of the first arm, and further comprising a second wing portion separated from the first wing portion and extending from one of the opposing sides of the second arm and the second wing portion sharing the interior surface of the second arm, wherein one or more of the ultrasonic sensors are coupled to the interior surface of the second wing portion, and wherein one or more of the trackable elements are coupled to the second wing portion.

10. The tracking apparatus of claim 9, wherein the body includes a first distal end at the first arm, an opposing second distal end at the second arm, and a midpoint between the first and the second distal ends, wherein the first wing portion is located between the first distal end and the midpoint of the body, and wherein the second wing portion is located between the midpoint and the second distal end of the body, and wherein the first distal end and the second distal end of the body are spaced from one another to define an opening configured to receive the patient limb.

11. The tracking apparatus of claim 1, wherein the wing portion shares the exterior surface of the at least one first and second arm.

12. The tracking apparatus of claim 1, further comprising a cushion coupled to the interior surface of the first and second arms and the interior surface of the wing portion, wherein the cushion is configured to contact the patient limb.

13. The tracking apparatus of claim 12, further compris- ing a control unit coupled to the cushion and configured to adjust a size of the cushion.

14. The tracking apparatus of claim 1, wherein the one or more controllers are configured to determine an integrity of contact between the tracking apparatus and the patient limb based on the ultrasonic waves received by at least one of the one or more ultrasonic sensors coupled to the interior surface of the first arm, the one or more ultrasonic sensors coupled to the interior surface of the second arm, and the one or more ultrasonic sensors coupled to the interior surface of the wing portion.

15. The tracking apparatus of claim 14, wherein the one or more controllers are configured to adjust at least one of the one or more ultrasonic sensors coupled to the interior surface of the first arm, the one or more ultrasonic sensors coupled to the interior surface of the second arm, and the one or more ultrasonic sensors coupled to the interior surface of the wing portion in response to determining the integrity of contact.

16. The tracking apparatus of claim 14, further comprising:

a cushion coupled to the interior surface of the first and second arms and the interior surface of the wing portion, wherein the cushion is configured to contact the patient limb; and a control unit coupled to the cushion and configured to adjust a size of the cushion, wherein the control unit is configured to adjust the size of the cushion in response to the one or more controllers determining the integrity of contact.

17. The tracking apparatus of claim 1, further comprising:

a light emitter configured to emit light to the patient limb; and an optical sensor configured to sense light reflected from the patient limb;

wherein the one or more controllers are coupled to the optical sensor and configured to determine an integrity of contact between the tracking apparatus and the patient limb based on the light sensed by the optical sensor.

18. The tracking apparatus of claim 1, wherein:

the one or more controllers are configured to determine a shape of the bone based on the ultrasonic waves received by at least one of the one or more ultrasonic sensors coupled to the interior surface of the first arm, the one or more ultrasonic sensors coupled to the interior surface of the second arm, and the one or more ultrasonic sensors coupled to the interior surface of the wing portion; and a non-transitory memory coupled to the one or more controllers, the non-transitory memory configured to store the shape of the bone and the one or more controllers being configured to determine a position of the bone relative to the one or more trackable elements in a coordinate system of the tracking apparatus based on the shape of the bone.

19. A tracking system for tracking a bone of a patient limb, the tracking system comprising:

a tracking apparatus comprising:

a body configured to couple to the patient limb and comprising first and second arms each including an exterior surface, an opposing interior surface, and opposing sides connecting the exterior and interior surfaces, wherein a hinge connects the first arm and the second arm such that the first arm and the second arm are rotatably moveable relative to one another relative to the hinge, and wherein a sensor is configured to sense a relationship between the first and second arms;

a wing portion extending from at least one of the opposing sides of at least one of the first and second arms and the wing portion sharing the interior surface of at least one of the first and second arms;

one or more ultrasonic sensors coupled to the interior surface of the body first arm, one or more ultrasonic sensors coupled to the interior surface of the second arm, and one or more ultrasonic sensors coupled to the interior surface of the wing portion, each being configured to transmit ultrasonic waves to and receive ultrasonic waves from the bone; and one or more trackable elements coupled to the body and the wing portion;

a localizer configured to sense the one or more of the trackable elements of the tracking apparatus; and one or more controllers coupled to the localizer and configured to determine:

a relationship between the one or more of the ultrasonic sensors of the first arm and the one or more of the ultrasonic sensors of the second arm;

a position of the bone relative to the one or more of the trackable elements in a coordinate system of the tracking apparatus based on the ultrasonic waves received by the one or more ultrasonic sensors;

a position of the one or more of the trackable elements in a coordinate system of the localizer based on sensing of the one or more trackable elements by the localizer; and the position of the bone in a coordinate system of the localizer.

20. A surgical system comprising:

a robotic manipulator comprising a tracker and an end effector including an energy applicator;

a tracking apparatus for tracking a bone of a patient limb, the tracking apparatus comprising:

a body configured to couple to the patient limb and comprising first and second arms each including an exterior surface, an opposing interior surface, and opposing sides connecting the exterior and interior surfaces, wherein a hinge connects the first arm and the second arm such that the first arm and the second arm are rotatably moveable relative to one another relative to the hinge, and wherein a sensor is configured to sense a relationship between the first and second arms;

a wing portion integrally formed with the body and extending from at least one of the opposing sides of at least one of the first and second arms and the wing portion sharing the interior surface of at least one of the first and second arms;

one or more ultrasonic sensors coupled to the interior surface of the first arm, one or more ultrasonic sensors coupled to the interior surface of the second arm, and one or more ultrasonic sensors coupled to the interior surface of the wing portion, each being configured to transmit ultrasonic waves to and receive ultrasonic waves from the bone; and one or more trackable elements coupled to the body and the wing portion;

a localizer configured to sense the tracker on the robotic manipulator and the one or more of the trackable elements of the tracking apparatus; and one or more controllers coupled to the localizer and configured to determine:

a relationship between the one or more of the ultrasonic sensors of the first arm and the one or more of the ultrasonic sensors of the second arm;

a position of the bone relative to the one or more of the trackable elements in a coordinate system of the tracking apparatus based on the ultrasonic waves received by the one or more ultrasonic sensors;

a position of the one or more of the trackable elements in a coordinate system of the localizer based on the sensing of the one or more trackable elements by the localizer;

the position of the bone in a coordinate system of the localizer; and a position of the energy applicator relative to the bone.

* * * * *